(12) United States Patent
Martin et al.

(10) Patent No.: US 11,976,263 B2
(45) Date of Patent: May 7, 2024

(54) CELL CULTURE INSERT

(71) Applicant: CORNING INCORPORATED, Corning, NY (US)

(72) Inventors: Gregory Roger Martin, Acton, ME (US); Allison Jean Tanner, Portsmouth, NH (US)

(73) Assignee: CORNING INCORPORATED, Corning, NY (US)

( * ) Notice: Subject to any disclaimer, the term of this patent is extended or adjusted under 35 U.S.C. 154(b) by 43 days.

(21) Appl. No.: 17/691,511

(22) Filed: Mar. 10, 2022

(65) Prior Publication Data
US 2022/0195366 A1   Jun. 23, 2022

Related U.S. Application Data

(63) Continuation of application No. 15/492,730, filed on Apr. 20, 2017, now abandoned, which is a continuation of application No. PCT/US2015/058053, filed on Oct. 29, 2015.

(60) Provisional application No. 62/069,996, filed on Oct. 29, 2014.

(51) Int. Cl.
  *C12M 1/32*  (2006.01)
  *C12M 1/12*  (2006.01)
  *C12M 3/00*  (2006.01)

(52) U.S. Cl.
  CPC ............ *C12M 25/04* (2013.01); *C12M 21/08* (2013.01); *C12M 23/12* (2013.01)

(58) Field of Classification Search
  CPC .............................. C12M 23/12; C12M 25/04
  See application file for complete search history.

(56) References Cited

U.S. PATENT DOCUMENTS

| | | |
|---|---|---|
| 2,947,116 A | 8/1960 | Wilton et al. |
| 3,630,849 A | 12/1971 | David et al. |
| 4,382,685 A | 5/1983 | Pearson |
| 4,498,785 A | 2/1985 | de Bruyne |
| 4,534,656 A | 8/1985 | de Bruyne |
| 4,670,396 A | 6/1987 | Bear et al. |
| 4,760,028 A | 7/1988 | de Bruyne et al. |
| 4,927,764 A | 5/1990 | Lyman et al. |
| 4,980,293 A | 12/1990 | Jeffs |
| 5,047,347 A | 9/1991 | Cline |
| 5,151,366 A | 9/1992 | Serkes et al. |

(Continued)

FOREIGN PATENT DOCUMENTS

| | | |
|---|---|---|
| AU | 2004256209 A1 | 1/2005 |
| CA | 2558946 A1 | 1/2005 |

(Continued)

OTHER PUBLICATIONS

Liu et al. "Quasi-spherical microwells on superhydrophobic substrates for long term culture of multicellular spheroids and high throughput assays" Biomaterials and Cancer 35 (2014) pp. 6060-6068.

(Continued)

*Primary Examiner* — Jonathan M Hurst
(74) *Attorney, Agent, or Firm* — Chandra J. Duncan

(57) ABSTRACT

A cell culture insert for use in culturing cells to promote the formation of spheroids and methods of using these spheroid-promoting cell culture inserts. The cell culture insert includes a porous membrane and one or more sidewalls that are non-adherent to cells and cause the cells in the insert to associate with each other and form spheroids.

11 Claims, 7 Drawing Sheets

(56) References Cited

U.S. PATENT DOCUMENTS

| | | |
|---|---|---|
| 5,171,994 A | 12/1992 | Bahraman |
| 5,171,995 A | 12/1992 | Gast et al. |
| 5,240,854 A | 8/1993 | Berry et al. |
| 5,272,084 A | 12/1993 | O'Connell et al. |
| 5,319,436 A | 6/1994 | Manns et al. |
| 5,374,557 A | 12/1994 | Verma |
| 5,398,837 A | 3/1995 | Degrassi |
| 5,487,872 A | 1/1996 | Hafeman et al. |
| 5,554,536 A | 9/1996 | Rising |
| 5,598,262 A | 1/1997 | Jutard et al. |
| 5,665,562 A | 9/1997 | Cook |
| 5,693,537 A | 12/1997 | Wilson et al. |
| 5,707,869 A | 1/1998 | Wolf et al. |
| 5,710,043 A | 1/1998 | Pay |
| 5,736,397 A | 4/1998 | Garcia et al. |
| 5,759,494 A | 6/1998 | Szlosek |
| 5,766,949 A | 6/1998 | Liau et al. |
| 5,772,905 A | 6/1998 | Chou |
| 5,783,440 A | 7/1998 | Stevens |
| 5,792,653 A | 8/1998 | Weibezahn et al. |
| 5,858,309 A | 1/1999 | Mathus et al. |
| 5,972,694 A | 10/1999 | Mathus |
| 6,030,829 A | 2/2000 | Dannoux et al. |
| 6,039,972 A | 3/2000 | Barlow et al. |
| 6,306,646 B1 | 10/2001 | Saad et al. |
| 6,348,999 B1 | 2/2002 | Summersgill et al. |
| 6,514,464 B1 | 2/2003 | Knebel |
| 6,521,451 B2 | 2/2003 | Potter |
| 6,567,675 B1 | 5/2003 | Rosen et al. |
| 6,767,607 B2 | 7/2004 | Tanner et al. |
| 6,811,752 B2 | 11/2004 | Barbera-Guillem |
| 6,908,767 B2 | 6/2005 | Bader |
| 7,470,424 B2 | 12/2008 | Kataoka et al. |
| 7,547,547 B2 | 6/2009 | Dang et al. |
| 7,674,346 B2 | 3/2010 | Clements et al. |
| 7,687,262 B2 | 3/2010 | Cattadoris |
| 7,691,369 B2 | 4/2010 | Kataoka et al. |
| 7,727,759 B2 | 6/2010 | Ozawa et al. |
| 7,745,209 B2 | 6/2010 | Martin et al. |
| 7,745,210 B2 | 6/2010 | Martin |
| 7,800,749 B2 | 9/2010 | Leblanc et al. |
| 7,897,379 B2 | 3/2011 | Kenney et al. |
| 7,919,319 B2 | 4/2011 | Jervis et al. |
| 8,053,230 B2 | 11/2011 | Whittlinger |
| 8,143,053 B2 | 3/2012 | Yerbic |
| 8,148,152 B2 | 4/2012 | Kolossov et al. |
| 8,158,426 B2 | 4/2012 | Wilson et al. |
| 8,158,427 B2 | 4/2012 | Wilson et al. |
| 8,163,537 B2 | 4/2012 | Martin et al. |
| 8,168,432 B2 | 5/2012 | Wilson et al. |
| 8,178,345 B2 | 5/2012 | Bennett et al. |
| 8,273,572 B2 | 9/2012 | Martin et al. |
| 8,318,479 B2 | 11/2012 | Domansky et al. |
| 8,415,144 B2 | 4/2013 | Wilson et al. |
| 8,470,589 B2 | 6/2013 | Martin et al. |
| D685,497 S | 7/2013 | Kenney et al. |
| 8,486,692 B2 | 7/2013 | Simon |
| 8,597,597 B2 | 12/2013 | Deutsch et al. |
| 8,617,879 B2 | 12/2013 | Yu et al. |
| 8,697,443 B2 | 4/2014 | Wilson et al. |
| 8,759,017 B2 | 6/2014 | Owen et al. |
| 8,778,669 B2 | 7/2014 | Lacey et al. |
| 8,846,399 B2 | 9/2014 | Martin et al. |
| 8,906,685 B2 | 12/2014 | Takayama et al. |
| 8,932,544 B2 | 1/2015 | Mueller et al. |
| 9,039,883 B2 | 5/2015 | Guerrieri et al. |
| 9,040,293 B2 | 5/2015 | Gulzow et al. |
| 9,045,721 B2 | 6/2015 | Martin et al. |
| 9,068,281 B2 | 6/2015 | Wu et al. |
| 9,126,199 B2 | 9/2015 | Moritz et al. |
| 9,169,460 B2 | 10/2015 | Cecchi |
| D748,812 S | 2/2016 | Kenney et al. |
| 9,260,684 B1 | 2/2016 | Egeler et al. |
| 9,260,695 B2 | 2/2016 | Crowley et al. |
| 9,389,187 B2 | 7/2016 | Furnas |
| 9,436,990 B2 | 9/2016 | Otani et al. |
| 9,493,733 B2 | 11/2016 | Giles |
| 9,494,577 B2 | 11/2016 | McGarr et al. |
| 9,573,128 B1 | 2/2017 | McClelland |
| 9,587,213 B2 | 3/2017 | Morgan et al. |
| 9,636,680 B2 | 5/2017 | Fattinger et al. |
| 9,732,317 B2 | 8/2017 | Wilson |
| 9,790,465 B2 | 10/2017 | Bennett et al. |
| 9,845,451 B2 | 12/2017 | Martin et al. |
| 9,862,918 B2 | 1/2018 | Ito |
| 9,933,373 B2 | 4/2018 | Vild et al. |
| 10,067,065 B1 | 9/2018 | Alam et al. |
| 10,254,274 B2 | 4/2019 | Miklas et al. |
| 11,441,121 B2 | 9/2022 | Bennett et al. |
| 11,613,722 B2 | 3/2023 | Martin et al. |
| 2002/0022219 A1 | 2/2002 | Clements et al. |
| 2002/0172621 A1 | 11/2002 | Barbera-Guillem |
| 2003/0031829 A1 | 2/2003 | Tanner et al. |
| 2003/0104494 A1 | 6/2003 | Ravkin et al. |
| 2003/0183958 A1 | 10/2003 | Goff et al. |
| 2003/0186217 A1 | 10/2003 | Bader |
| 2003/0215941 A1 | 11/2003 | Campbell et al. |
| 2004/0091397 A1 | 5/2004 | Picard |
| 2004/0101955 A1 | 5/2004 | Whitley |
| 2004/0125266 A1 | 7/2004 | Miyauchi et al. |
| 2004/0216835 A1 | 11/2004 | Tanner et al. |
| 2004/0259242 A1 | 12/2004 | Malinge et al. |
| 2004/0259423 A1 | 12/2004 | Elbaz et al. |
| 2005/0032208 A1 | 2/2005 | Oh et al. |
| 2005/0047971 A1 | 3/2005 | Clements et al. |
| 2005/0074873 A1 | 4/2005 | Shanler et al. |
| 2005/0112030 A1 | 5/2005 | Gaus |
| 2005/0116717 A1 | 6/2005 | Dransfield et al. |
| 2005/0147959 A1 | 7/2005 | Frondoza et al. |
| 2006/0110822 A1 | 5/2006 | Robbins et al. |
| 2006/0234370 A1 | 10/2006 | Korpinen et al. |
| 2006/0252044 A1 | 11/2006 | Okumura et al. |
| 2006/0292654 A1 | 12/2006 | Reardon |
| 2007/0178441 A1 | 8/2007 | Li |
| 2007/0216897 A1 | 9/2007 | Sonda |
| 2008/0003671 A1 | 1/2008 | Martin |
| 2008/0009027 A1 | 1/2008 | Fraker et al. |
| 2008/0118974 A1 | 5/2008 | Martin et al. |
| 2008/0206857 A1 | 8/2008 | Kenney et al. |
| 2008/0268515 A1 | 10/2008 | Cullimore et al. |
| 2008/0297784 A1 | 12/2008 | Leblanc et al. |
| 2008/0299649 A1 | 12/2008 | Martin et al. |
| 2008/0300278 A1 | 12/2008 | Torrens et al. |
| 2009/0017540 A1 | 1/2009 | Nishio et al. |
| 2009/0018033 A1 | 1/2009 | Morgan et al. |
| 2009/0029462 A1 | 1/2009 | Beardsley et al. |
| 2009/0037293 A1 | 2/2009 | Unger et al. |
| 2009/0170190 A1 | 7/2009 | Nishi et al. |
| 2009/0191620 A1 | 7/2009 | Martin et al. |
| 2009/0288963 A1 | 11/2009 | Guerrieri et al. |
| 2009/0298164 A1 | 12/2009 | Cattadoris et al. |
| 2009/0298166 A1 | 12/2009 | Fang et al. |
| 2010/0055774 A1 | 3/2010 | Wilson |
| 2010/0068793 A1 | 3/2010 | Ungrin et al. |
| 2010/0074515 A1 | 3/2010 | Zhao et al. |
| 2010/0093075 A1 | 4/2010 | Mueller |
| 2010/0112014 A1 | 5/2010 | Gilbert et al. |
| 2010/0112684 A1 | 5/2010 | Lee et al. |
| 2010/0119418 A1 | 5/2010 | Clements et al. |
| 2010/0170790 A1 | 7/2010 | Takahashi et al. |
| 2010/0190197 A1 | 7/2010 | Martin et al. |
| 2010/0197013 A1 | 8/2010 | Kamp et al. |
| 2010/0247386 A1 | 9/2010 | Deutsch et al. |
| 2010/0273258 A1 | 10/2010 | Lannutti et al. |
| 2010/0296084 A1 | 11/2010 | Berg et al. |
| 2010/0297600 A1 | 11/2010 | Cecchi |
| 2011/0086375 A1 | 4/2011 | Ungrin et al. |
| 2011/0097790 A1 | 4/2011 | Yerbic |
| 2011/0129923 A1 | 6/2011 | Wilson et al. |
| 2011/0229961 A1 | 9/2011 | Higashi et al. |
| 2012/0064627 A1 | 3/2012 | Khine et al. |
| 2012/0129208 A1 | 5/2012 | Khine et al. |
| 2012/0129257 A1 | 5/2012 | Yu et al. |
| 2012/0219572 A1 | 8/2012 | Prockop et al. |

(56) References Cited

U.S. PATENT DOCUMENTS

| | | |
|---|---|---|
| 2013/0052331 A1 | 2/2013 | Kram et al. |
| 2013/0122539 A1 | 5/2013 | Li et al. |
| 2013/0122580 A1 | 5/2013 | Tsukada et al. |
| 2013/0143254 A1 | 6/2013 | Thomas et al. |
| 2013/0164848 A1 | 6/2013 | Munaka et al. |
| 2013/0203159 A1 | 8/2013 | Itoh et al. |
| 2013/0344598 A1 | 12/2013 | Nistor |
| 2014/0004086 A1 | 1/2014 | Peak |
| 2014/0027784 A1 | 1/2014 | Wada et al. |
| 2014/0099717 A1 | 4/2014 | Fraker et al. |
| 2014/0106394 A1 | 4/2014 | Ko et al. |
| 2014/0106452 A1 | 4/2014 | Vukasinovic |
| 2014/0120573 A1 | 5/2014 | Tavana et al. |
| 2014/0178992 A1 | 6/2014 | Nakashima et al. |
| 2014/0221225 A1 | 8/2014 | Danen et al. |
| 2014/0226004 A1 | 8/2014 | Son et al. |
| 2014/0227784 A1 | 8/2014 | Ejiri et al. |
| 2014/0240489 A1 | 8/2014 | Furnas |
| 2014/0315296 A1 | 10/2014 | Wilson |
| 2014/0322806 A1 | 10/2014 | Bennett et al. |
| 2015/0004686 A1 | 1/2015 | Goral et al. |
| 2015/0064738 A1 | 3/2015 | Tsukada et al. |
| 2015/0072405 A1 | 3/2015 | Ito |
| 2015/0184119 A1 | 7/2015 | Tsukada et al. |
| 2015/0247112 A1 | 9/2015 | Orr et al. |
| 2016/0003796 A1 | 1/2016 | Kranbuehl |
| 2016/0017267 A1 | 1/2016 | Hansen et al. |
| 2016/0040120 A1 | 2/2016 | Gottwald et al. |
| 2016/0137962 A1 | 5/2016 | Ejiri et al. |
| 2016/0194588 A1 | 7/2016 | Guenat et al. |
| 2016/0216250 A1 | 7/2016 | Ritter et al. |
| 2016/0250631 A1 | 9/2016 | Kang et al. |
| 2017/0067009 A1 | 3/2017 | Sloane et al. |
| 2017/0067019 A1 | 3/2017 | Ho |
| 2017/0073625 A1 | 3/2017 | Kasuto et al. |
| 2017/0226455 A1 | 8/2017 | Fang et al. |
| 2017/0267959 A1 | 9/2017 | Martin et al. |
| 2017/0283757 A1 | 10/2017 | Carter et al. |
| 2017/0306281 A1 | 10/2017 | Martin et al. |
| 2017/0342363 A1 | 11/2017 | Fang et al. |
| 2018/0166743 A1 | 6/2018 | Lee et al. |
| 2018/0201888 A1 | 7/2018 | Miwa et al. |
| 2018/0301754 A1 | 10/2018 | Badding et al. |
| 2019/0006707 A1 | 1/2019 | Sakamoto et al. |
| 2020/0064197 A1 | 2/2020 | Furnas |
| 2020/0131461 A1 | 4/2020 | Martin et al. |
| 2020/0199006 A1 | 6/2020 | Jain et al. |
| 2020/0239854 A1 | 7/2020 | Ayano et al. |
| 2021/0062126 A1 | 3/2021 | Martin et al. |
| 2022/0220434 A1 | 7/2022 | Martin et al. |
| 2022/0259540 A1 | 8/2022 | Li et al. |

FOREIGN PATENT DOCUMENTS

| | | |
|---|---|---|
| CA | 2679011 A1 | 9/2008 |
| CA | 2848875 A1 | 3/2013 |
| CN | 2186755 Y | 1/1995 |
| CN | 1168921 A | 12/1997 |
| CN | 1234112 A | 11/1999 |
| CN | 1867663 A | 11/2006 |
| CN | 1875093 A | 12/2006 |
| CN | 201626959 U | 11/2010 |
| CN | 101978041 A | 2/2011 |
| CN | 102105578 A | 6/2011 |
| CN | 102257123 A | 11/2011 |
| CN | 102449135 A | 5/2012 |
| CN | 102687023 A | 9/2012 |
| CN | 202450098 U | 9/2012 |
| CN | 202849407 U | 4/2013 |
| CN | 103080294 A | 5/2013 |
| CN | 103119151 A | 5/2013 |
| CN | 203513696 U | 4/2014 |
| CN | 103814125 A | 5/2014 |
| CN | 204608026 U | 9/2015 |
| CN | 204702760 U | 10/2015 |
| CN | 204714819 U | 10/2015 |
| CN | 204752742 U | 11/2015 |
| CN | 204803327 U | 11/2015 |
| CN | 205170866 U | 4/2016 |
| CN | 205669029 U | 11/2016 |
| CN | 205839030 U | 12/2016 |
| CN | 205990396 U | 3/2017 |
| CN | 107109340 A | 8/2017 |
| CN | 107109341 A | 8/2017 |
| CN | 107208025 A | 9/2017 |
| CN | 107460125 A | 12/2017 |
| DE | 8309876 U1 | 12/1983 |
| DE | 10019862 A1 | 11/2001 |
| DE | 202006017853 U1 | 1/2007 |
| DE | 102009005526 A1 | 7/2010 |
| DE | 102014214077 A1 | 1/2016 |
| DE | 102014017728 A1 | 6/2016 |
| EP | 0307048 A2 | 3/1989 |
| EP | 0605527 A1 | 7/1994 |
| EP | 0681846 A2 | 11/1995 |
| EP | 0800571 A2 | 10/1997 |
| EP | 0834552 A1 | 4/1998 |
| EP | 0965633 A1 | 12/1999 |
| EP | 1181349 A1 | 2/2002 |
| EP | 1348533 A2 | 10/2003 |
| EP | 1445022 A2 | 8/2004 |
| EP | 1988152 A1 | 11/2008 |
| EP | 2032262 A2 | 3/2009 |
| EP | 2617807 A1 | 7/2013 |
| EP | 2653531 A1 | 10/2013 |
| EP | 2759592 A1 | 7/2014 |
| EP | 2896684 A1 | 7/2015 |
| EP | 3081627 A1 | 10/2016 |
| EP | 3296018 A1 | 3/2018 |
| EP | 3351615 A1 | 7/2018 |
| EP | 3372666 A1 | 9/2018 |
| GB | 2147100 A | 5/1985 |
| JP | 03-139350 A | 6/1991 |
| JP | 06-038734 A | 2/1994 |
| JP | 06-327462 A | 11/1994 |
| JP | 09-173049 A | 7/1997 |
| JP | 09-234811 A | 9/1997 |
| JP | 10-210866 A | 8/1998 |
| JP | 10-210966 A | 8/1998 |
| JP | 2001-106749 A | 4/2001 |
| JP | 2003-135056 A | 5/2003 |
| JP | 2003-180335 A | 7/2003 |
| JP | 2004-129558 A | 4/2004 |
| JP | 2004-535829 A | 12/2004 |
| JP | 2005-080660 A | 3/2005 |
| JP | 2006-121991 A | 5/2006 |
| JP | 2006-191809 A | 7/2006 |
| JP | 2007-510429 A | 4/2007 |
| JP | 3139350 U | 2/2008 |
| JP | 2009-017810 A | 1/2009 |
| JP | 2009-050194 A | 3/2009 |
| JP | 2009-183288 A | 8/2009 |
| JP | 2009-542230 A | 12/2009 |
| JP | 2010-088347 A | 4/2010 |
| JP | 2010-104327 A | 5/2010 |
| JP | 2010-518879 A | 6/2010 |
| JP | 2010-158214 A | 7/2010 |
| JP | 2011-509686 A | 3/2011 |
| JP | 2011-521642 A | 7/2011 |
| JP | 2011-172533 A | 9/2011 |
| JP | 2011-528226 A | 11/2011 |
| JP | 2012-249547 A | 12/2012 |
| JP | 2013-055911 A | 3/2013 |
| JP | 2014-132869 A | 7/2014 |
| JP | 2015-012827 A | 1/2015 |
| JP | 2015-029431 A | 2/2015 |
| JP | 2015-073520 A | 4/2015 |
| JP | 2016-002023 A | 1/2016 |
| JP | 5845185 B2 | 1/2016 |
| JP | 2016-093149 A | 5/2016 |
| JP | 2016-136920 A | 8/2016 |
| JP | 2016-136921 A | 8/2016 |
| JP | 2017-532970 A | 11/2017 |
| JP | 2018-108032 A | 7/2018 |

(56) References Cited

FOREIGN PATENT DOCUMENTS

| KR | 10-2014-0113139 | A  | 9/2014 |
|---|---|---|---|
| KR | 10-2014-0125662 | A  | 10/2014 |
| KR | 10-2017-0008539 | A  | 1/2017 |
| WO | 92/07063 | A2 | 4/1992 |
| WO | 93/07258 | A1 | 4/1993 |
| WO | 96/21851 | A2 | 7/1996 |
| WO | 98/15355 | A2 | 4/1998 |
| WO | 98/31466 | A1 | 7/1998 |
| WO | 01/80997 | A1 | 11/2001 |
| WO | 01/92462 | A1 | 12/2001 |
| WO | 2004/044120 | A2 | 5/2004 |
| WO | 2004/094060 | A1 | 11/2004 |
| WO | 2005/047464 | A2 | 5/2005 |
| WO | 2006/043267 | A1 | 4/2006 |
| WO | 2007/015770 | A1 | 2/2007 |
| WO | 2007/097120 | A1 | 8/2007 |
| WO | 2008/006104 | A2 | 1/2008 |
| WO | 2008/008149 | A2 | 1/2008 |
| WO | 2008/106771 | A1 | 9/2008 |
| WO | 2008/118500 | A1 | 10/2008 |
| WO | 2008/140295 | A1 | 11/2008 |
| WO | 2008/149039 | A2 | 12/2008 |
| WO | 2008/153783 | A1 | 12/2008 |
| WO | 2009/094125 | A2 | 7/2009 |
| WO | 2009/148509 | A1 | 12/2009 |
| WO | 2009/148512 | A2 | 12/2009 |
| WO | 2010/008566 | A2 | 1/2010 |
| WO | 2010/042072 | A1 | 4/2010 |
| WO | 2010/069589 | A1 | 6/2010 |
| WO | 2012/036011 | A1 | 3/2012 |
| WO | 2012/077683 | A1 | 6/2012 |
| WO | 2012/170232 | A1 | 12/2012 |
| WO | 2013/042360 | A1 | 3/2013 |
| WO | 2013/108293 | A1 | 7/2013 |
| WO | 2013/116449 | A1 | 8/2013 |
| WO | 2014/042162 | A1 | 3/2014 |
| WO | 2014/072432 | A1 | 5/2014 |
| WO | 2014/140181 | A1 | 9/2014 |
| WO | 2014/156455 | A1 | 10/2014 |
| WO | 2014/165273 | A1 | 10/2014 |
| WO | 2014/171782 | A1 | 10/2014 |
| WO | 2014/179196 | A1 | 11/2014 |
| WO | 2014/196204 | A1 | 12/2014 |
| WO | 2015/033507 | A1 | 3/2015 |
| WO | 2015/061907 | A1 | 5/2015 |
| WO | 2015/087369 | A1 | 6/2015 |
| WO | 2016/020992 | A1 | 2/2016 |
| WO | 2016/064757 | A1 | 4/2016 |
| WO | 2016/069885 | A1 | 5/2016 |
| WO | 2016/069892 | A1 | 5/2016 |
| WO | 2016/069895 | A1 | 5/2016 |
| WO | 2016/069917 | A1 | 5/2016 |
| WO | 2016/069930 | A1 | 5/2016 |
| WO | 2016/157322 | A1 | 10/2016 |
| WO | 2017/025584 | A1 | 2/2017 |
| WO | 2017/047735 | A1 | 3/2017 |
| WO | 2017/077163 | A1 | 5/2017 |
| WO | 2017/142410 | A1 | 8/2017 |
| WO | 2018/068034 | A1 | 4/2018 |
| WO | 2018/200893 | A1 | 11/2018 |
| WO | 2019/010401 | A1 | 1/2019 |
| WO | 2019/014621 | A1 | 1/2019 |
| WO | 2019/014627 | A1 | 1/2019 |
| WO | 2019/014635 | A1 | 1/2019 |
| WO | 2019/014636 | A1 | 1/2019 |
| WO | 2019/178039 | A1 | 9/2019 |

OTHER PUBLICATIONS

Liu et al; "Advanced Micromachining of Concave Microwells for Long Term On-Chip Culture of Multicellular Tumour Spheroids", ACS Appl. Mater. Interfaces, 2014, 35 Pages.
Lonza Inc., "SeaPrep Agarose: An Ultralow Gelling, Soft Agarose", Available Online at <http://www.lonzabio.jp/catalog/pdf/pd/PD031.pdf>, 2007, pp. 1-4.
Lovett et al. "Vascularization Strategies for Tissue Engineering" Tissue Engineering Part B, 2009, vol. 15, No. 3, pp. 353-370.
Lquid Surge Control, LLC; "The Latest in Drop-In Baffle Technology"; 2 Pages; (2019).
Lu et al. "Galactosylated PVDF membrane promotes hepatocyte attachment and functional maintenance." Biomaterials 2003;24:4893-903.
Markovitz-Bishitz, "A polymer microstructure array for the formation, culturing, and high throughput drug screening of breast cancer spheroids" Biomaterials and Biotechnology 31 (2010) pp. 8436-8444.
Martin et al., "Agarose And Methylcellulose Hydrogel Blends For Nerve Regeneration Applications", J. Neural Eng., vol. 5, 2008, pp. 221-231.
Messner et al, Multi-cell type human liver microtissues for hepatotoxicity testing. Archives of Toxicology, Nov. 11, 2012, 5 pages.
Mimetas the Organ-On-A-Chip Company; "Organ-On-A-Chip Models for Science and Pharma"; 4 Pages; (Downloaded Mar. 9, 2020); https://mimetas.com/.
Mironov et al; "Organ Printing: Tissue Spheroids as Buliding Blocks" Biomaterials, 2009; 30 (12) 2164-2174.
Murphy et al; "3D Bioprinting of Tissues and Organs"; Nature Biotechnology, vol. 32, No. 8. Aug. 2014, pp. 773-785.
Nortis; "Bridging the Gap Between In Vitro and In Vivo Research"; 16 Pages; (2015); https://www.nortisbio.com/.
Organovo, "Pioneering Bioprinted Tissues to Treat Disease"; 2 Pages; (Downloaded Mar. 9, 2020) http://organovo.com/.
Otsuka et al, "Two-dimensional multiarray formation of hepatocyte spheroids on a microfabricated PEG-brush surface." ChemBioChem 2004; 5:850-855.
Polyimide: Japan Polyimide and Aromatic Polymers Study Group, 2010, pp. 364-371 Table 2.
Rezende et al, "Scalable Biofabrication of Tissue Spheroids for Organ Printing"; Sciverse Science Direct, Procedia CIRP 5, (2013) 276-281.
Sa et al. "Round-bottomed Honeycomb Microwells: Embryoid body shape correlates with stem cell fate" Journal of Developmental Biology and Tissue Engineering vol. 4(2), pp. 12-22, May 2012.
Sakai et al, "Large-scale preparation and function of porcine hepatocyte spheroids." Int J Artif Organs 1996; vol. 19, No. 5, pp. 294-301.
Sakai et al, "Technique for the Control of Spheroid Diameter Using Microfabricated Chips"; Sciencedirect, Acta Biomaterialia 3 (2007) 1033-1040.
Sakai et al; "Detachably Assembled Microfluidic Device for Perfusion Culture and Post-Culture Analysis of Spheroid Array"; Biotechnol. J. 2014, 9, 971-979.
Sakai et al; "Technique for the Control of Spheroid Diameter Using Microfabricated Chips"; Sciencedirect, Acta Biomaterials 3 (2007) 1033-1040.
Satoh et al, "A Pneumatic Pressure-Driven Multi-Throughput Microfluidic Circulation Culture System" Lab Chip, 2016, 16, 2339-2348.
Seldon et al; "Evaluation of Encapsulated Liver Cell Spheroids in a Fluidised-Bed Bioartificial Liver for Treatment of Ischaemic Acute Liver Failure in Pigs in the Translational Setting": PLOS One; Dec. 2013, vol. 8, Issue 12, 12 Pages.
Stemcell Technologies, Reproducible and Uniform Embryoid Bodies Using AggreWell Plates, StemCell Technologies, Version 3.0.0, Mar. 2011, Catalog #29146, pp. 1-28.
Tara; "Innovating Predictive Cardiac Physiology"; 4 Pages; (2019) http://tarabiosystems.com/.
The Lab Depot(Registered) Products for Discovery Lab Supplies; Shake Flasks, 3 and 4 Baffles Product Information; 5 Pages (2019).
Tissue Dynamics, "Disruptive Drug Development"; 3 Pages; (Downloaded Mar. 9, 2020); https://www.tissuedynamics.com/.
Tissuse; Technology, Available on (https://www.tissuse.com/en/technology/), Accessed May 11, 2021, 4 pages.
Tobe et al, "Receptor-mediated formation of multilayer aggregates of primary cultured adult rat hepatocytes on tactose-subsliluled polystyrene" Biochem Biophys Res Commun 1992; 184(1):225-230.

(56) References Cited

OTHER PUBLICATIONS

Tong et al, "Long-term culture of adult rat hepatocyte spheroids." Exp Cell Res 1992; 200:326-332.
Tung et al, "High-throughput 3D spheroid culture and drug testing using 384 hanging drop array" Analyst, 2011, 136 (3), 473-478.
Vinci et al. Advances in establishment and analysis of three-dimensional tumor spheroid-based functional assays for target validation and drug evaluation, BMC Biology 2012, 10:29.
Weegman et al, "Nutrient Regulation By Continuous Feeding Removes Limitations on Cell Yield in the Large-Scale Expansion of Mammalian Cell Spheroids"; PLOS One, 2013, vol. 8, Issue 10, e76611, 10 Pages.
Wikipedia, "Antiroll Tanks"; 3 Pages; Page Last Edited May 23, 2019.
Wrighton et al, "Forces of Change: Mechanics Underlying Formation of Functional 3D Organ Buds" Cell Stem Cell, May 7, 2015; 16(5): 453-454.
Xu et al, "Characterisation of some cytotoxic endpoints using rat liver and HepG2 spheroids as in vitro models and their application in hepatotoxicity studies. I. Glucose metabolism and enzyme release as cytotoxic markers." Toxicol Appl Pharmacol 2003; 189:100-111.
Yamada et al, "Efficient induction of hepatocyte spheroids in a suspension culture using a water-soluble synthetic polymer as an artificial matrix." J Biochem 1998; 123:1017-1023.
Yang et al., "An Agarose-Gel Based Method for Transporting Cell Lines", Current Chemical Genomics, vol. 3, Jan. 2009, pp. 50-53.
Zuidema et al., "Fabrication And Characterization Of Tunable Polysaccharide Hydrogel Blends For Neural Repair", Acta Biomaterialia, vol. 7, No. 4, Apr. 2011, pp. 1634-1643.
Achilli et al, "Advances in the Formation, Use and Understanding of Multi-Cellular Spheroids", Expert Opin. Biol. Ther. (2012) 12(10):1347-1360.
Alepee et al, "State-of-the-Art 3D Cultures (Organs-on-a-Chip) in Safety Testing and Pathophysiology"; Transatlantic Think Tank for Toxicology, T4 Workshop Report, Altex 31, 4/14, pp. 441-477, Retrieved From: http://dx.doi.org/10.14573/altex1406111 (Jul. 14, 2014).
Aline, "We Engineer Microfluidic Products" ; 7 Pages; (2020) https://alineinc.com/.
Anada et al; "An Oxygen-Permeable Spheroid Culture System for the Prevention of Central Hypoxia and Necrosis of Spheroids"; Biomaterials, 33, (2012) 8430-8441.
AxoSIM, Nerve-on-a-Chip Mini-Brain About Team; 6 Pages; (Downloaded Mar. 9, 2020); http://axosim.com/.
Bartosh et al; "Aggregation of Human Mesenchymal Stromal Cells (MSCS) Into 3D Spheroid Enhances Their AntiInflammatory Properties"; PNAS, Aug. 3, 2010, vol. 107, No. 31 pp. 13724-13729.
Bioivt Elevating Science(Registered); 6 Pages; (2020); http://www.hepregen.com/.
Brandrup et al., "Polymer Handbook", Fourth Edition, Wiley-Interscience Publication, , Permeability and diffusion data, 1999, 9 pages (Contributors; Preface).
Carver et al; Multicellular Tumor Spheroids as a Model for Assessing Delivery of Oligonucleotides in Three Dimensions; Molecular Therapy-Nucleic Acids (2014) 3, E153; 8 Pages.
Chen et al., "Microfluidic array for three-dimensional perfusion culture of human mammary epithelial cells." Biomed Microdevices, vol. 13 (2011), pp. 753-758.
Cheng et al, "MicroRNA-34a Targets Forkhead Box J2 to Modulate Differentiation of Endothelial Progenitor Cells in Response to Shear Stress", J Mol Cell Cardiol. 74 (2014) 4-12.
Choi et al., "Feasibility of a simple double-layered coculture system incorporating metabolic processes of the intestine and liver tissue: application to the analysis of benzo[a]pyrene toxicity" Toxicology in Vitro, vol. 18, pp. 393-402, 2004.
CN-BIO, "Transforming Drug Discovery and the Lives of Patients"; 5 Pages; (2020) http://cn-bio.com/.
Colazzo et al, "Shear Stress and VEGF Enhance Endothelial Differentiation of Human Adipose-Derived Stem Cells", Growth Factors, 2014, 32(5): 139-149.
Corning Life Sciences Product Portfolio; 5 Pages Saved Mar. 6, 2020.
Corning(Registered) HTS Transwell(Registered)-96 Tissue Culture Systems, Permeable Supports for High Throughput Screening Applications; 2 Pages (2004).
Curcio et al. "Mass transfer and metabolic reactions in hepatocyte spheroids cultured in rotating wall gas-permeable membrane system." Biomaterials 28 (2007) 5487-5497. (Year: 2007).
Dolznig et al, "Organotypic spheroid cultures to study tumor-stroma interaction during cancer development", Drug Discovery Today: Disease Models, 2011, 8(2-3):113-118.
Domansky et al, "Perfused Multiwell Plate for 30 Liver Tissue Engineering", Lab Chip, 2010, 10:51-58.
Elveflow; "Microfluidics Innovation Center"; 6 Pages; (Downloaded Mar. 9, 2020); https://www.elveflow.com.
Emulate, 6 Pages; (2019) https://emulatebio.com/.
Endo et al., "Gene transfection to spheroid culture system on micropatterned culture plate by polyplex nanomicelle: a novel platform of genetically-modified cell transplantation", Drug Deliv. and Transl. Res., 2012, vol. 2, p. 398-405.
Engelberg et al, "Essential operating principles for tumor spheroid growth", BMC Systems Biology 2008, 2:110, 19 pages.
Evenou et al. "Spontaneous Formation of Highly Functional Three-Dimensional Multilayer from Human Hepatoma Hep G2 Cells Cultured on an Oxygen-Permeable Polydimethylsiloxane Membrane." Tissue Engineering: Part C vol. 16, No. 2, 2010, pp. 311-318. (Year: 2010).
Friedrich et al. "Spheroid-based drug screen: considerations and practical approach." Nature protocols, 2009, vol. 4 No. 3, 309-323.
Fukuda et al, "Efficacy of a polyurethane foam/spheroid artificial liver by using human hepaloblastoma cell line (Hep G2)", Cell Transplantation, 2003, 12:51-58.
G-Plate: Accelerate your cell cultures to the next dimension, "An original cell culture model allowing for inland shaped 3D cell aggregates" 1 page, retrieved Sep. 8, 2015.
GeoCHEM Incorporated, Product Line; hllps://www.geocheminc.com, 4 Pages; (2020).
HμREL (Registered) Corporation, Bioanalytic Tools Company; 2 Pages; (2013); http://hurelcorp.com/.
Haycock, "3D cell culture: a review of current approaches and techniques", Methods Mol Biol, 2011; 695:1-15.
Hirschhaeuser et al., "Mulicellular tumor spheroids: An underestimated tool is catching up again." Journal of Biotechnology, 2010, 148, 3-15.
Howes et al; "3-Dimensional Culture Systems for Anit-Cancer Compound Profiling and High-Throughput Screening Reveal Increases in EGFR Inhibitor-Mediated Cytotoxicity Compared to Monolayer Culture Systems"; PLOS One; Sep. 2004, vol. 9, Issue 9, 11 Pages.
Hribar et al; "Nonlinear 3D Projection Printing of Concave Hydrogel Microstructures for Long-Term Multicellular Spheroid and Embryoid Body Culture"; Lab Chip, 2015, 15, 2412-2418.
Hsiao et al., "Effects of 3D Microwell Culture on Initial Fate Specification in Human Embryonic Stem Cells", Published in final edited form as AIChE J. vol. 60 No. 4, Apr. 2014, pp. 1225-1235.
Huang et al., "Preparation of dense Ta—LLZO/MgO composite Li-ion solid electrolyte: Sintering, microstructure, performance and the role of MgO", Journal of Energy Chemistry, vol. 39, 2019, pp. 8-16.
Hwang et al; "Microwell-Mediated Control of Embryoid Body Size Regulates Embryonic Stem Cell Fate via Differential Expression of WNT5A and WNT11"; PNAS; Oct. 6, 2009, vol. 106, No. 40, pp. 16978-16983.
Jeon et al, "Combined Effects of Flow-Induced Shear Stress and Micropatterned Surface Morphology on Neuronal Differentiation of Human Mesenchymal Stem Cells" J Biosci Bioeng, 2014, 117(2):242-247.
Jiang et al, "Shear Enhances Thrombopoiesis and Formation of Microparticles That Induce Megakaryocytic Differentiation of Stem Cells", Blood, Sep. 25, 2014; 124(13):2094-2103.
Junji Fukuda et al., "Hepatocyte Spheroid Arrays Inside Microwells Connected With Microchannels", Biomicrofluidics 5, 2011, pp. 10.

(56) References Cited

OTHER PUBLICATIONS

Kelm et al, "Method for generation of homogeneous multicellular tumor spheroids applicable to a wide variety of cell types", Biotechnology and Bioengineering 2003; 83(2):173-180.

Kim et al, "Shear Stress Induced by an Interstitial Level of Slow Flow Increases the Osteogenic Differentiation of Mesenchymal Stem Cells Through Taz Activation" PLoS ONE, Mar. 21, 2014; 9(3), e92427, 9 pages.

Koide et al, "Formation of multicellular spheroids composed of adult rat hepatocytes in dishes with positively charged surfaces and under other nonadherent environments", Exp Cell Res 1990; 186:227-235.

Koike et al. "Characterization of Embryo id Bodies of Mouse Embryonic Stem Cells Formed under Various Culture Conditions and Estimation of Differentiation Status of Such Bodies." Journal of Bioscience and Bioengineering vol. I 04, No. 4, 294-299. 2007. (Year: 2007).

Kunz-Schughart et al, "The use of 3-D cultures for high-throughput screening: the multicellular spheroid model", J Biomol Screen 2004, 9(4):273-285.

Kutsuzawa et al, "Highly Robust Protein Production by Co-Culture of CHO Spheroids Layered on Feeder Cells in Serum-Free Medium"; Colloid Polym Sci (2014) 292; 839-848.

Labusca, "Scaffold free 3D culture of mesenchymal stem cells; implications for regenerative medicine", J Transplant Stem Cel Biol 2015 2(1): 8.

Landry et al, "Spheroidal aggregate culture of rat liver cells: histotypic reorganization, biomatrix deposition, and maintenance of functional activities" J Cell Biol 1985; 101:914-923.

Lau et al., "Evaluation of a Novel in Vitro CAC0-2 Hepatocyte Hybrid System for Predicting In Vivo Oral Bioavailability" Drug Metabolism and Disposition, vol. 32, No. 9, pp. 937-942, 2004.

Lin et al., "La2Zr2O7 and MgO co-doped composite Li-Garnet solid electrolyte", Journal of Energy Chemistry, vol. 40, 2020, pp. 132-136.

Liquid Surge Control, LLC; "The Latest in Drop-In Baffle Technology"; 2 Pages; (2019).

"Identification grid for microplates", Rtreived from: https://www.kisker-biotech.com/frontoffice/product?produitId=0N-27-11, 2 pages, 2021.

CELL CULTURE INSERT

This application is a continuation of U.S. patent application Ser. No. 15/492,730 filed on Apr. 20, 2017, which is a continuation application of International Patent Application Serial No. PCT/US15/58053 filed on Oct. 29, 2015, which claims the benefit of priority to U.S. Provisional Application Ser. No. 62/069,996, filed on Oct. 29, 2014, the contents of which are relied upon and incorporated herein by reference in their entirety, and the benefit of priority under 35 U.S.C. § 120 is hereby claimed.

FIELD

The present disclosure relates to apparatuses, systems and methods for culturing cells.

TECHNICAL BACKGROUND

The present disclosure relates generally to cell culture inserts for use in culturing cells to promote the formation of spheroids and methods of using these spheroid-promoting cell culture inserts. Spheroids are three-dimensional (3D) cell clusters that can provide more in vivo-like functions to the cells than cells cultured as monolayers in 2D cell culture systems. For certain cell types, such as hepatocytes, spheroids can attain and retain better in vivo-like functionality than their 2D cultured counterparts.

BRIEF SUMMARY

In accordance with various embodiments of the present disclosure, cell culture inserts for use in culturing cells to promote the formation of spheroids and methods of using these spheroid-promoting cell culture inserts are described. In some embodiments, a cell culture insert as described herein can be nested in another cell culture insert or another cell culture insert can be nested in a cell culture insert as described herein.

In various embodiments, the disclosure describes a cell culture insert having a body and a porous membrane. The body has a first open end, a second end wherein the second end defines an opening having a diametric dimension in a range from 100 µm to 1000 µm (e.g., 100, 200, 300, 400, 500, 600, 700, 800, 900, 1000 and all values and ranges therein between; e.g., 200 to 500, 200 to 700, 400 to 600, etc.), and one or more sidewalls extending from the first open end to the second end. The one or more sidewalls, or a portion thereof, are sloped (e.g., greater than 5 degrees from perpendicular relative to first or second ends; e.g., >10°, >20°, >30°, >40°, >50°, etc.). The sidewalls, if sloped, are preferably sloped such that the diameter at the second is less than the diameter at the first open end. A porous membrane is disposed over the opening of the second end.

In various embodiments, the disclosure describes a cell culture insert having a body and a porous membrane. The body has a first open end, a second end wherein the second end defines an opening, and one or more sidewalls extending from the first open end to the second end. The one or more sidewalls, or a portion thereof, are sloped. The porous membrane is disposed over the opening of the second end and is non-adherent to cells.

In various embodiments, the disclosure describes a permeable support device configured to be at least partially inserted into a reservoir of a cell culture device. The permeable support device comprises a first well having a tapered shape and bottom at least partially defined by a first permeable support.

In various embodiments, the disclosure described a cell culture insert. The insert includes a body having a first open end, a second end, and one or more sidewalls extending from the first open end to the second end. The second end comprises a substrate having an array of microwells defining wells with a porous membrane at the bottom, wherein at least a portion of a substrate having an array of microwells defining a well is sloped.

In various embodiments, the disclosure describes a nested permeable support device comprising a first well having a tapered shape and a bottom portion at least partially defined by a first permeable support, and a reservoir having a bottom located below the first well. In embodiments the reservoir is made from gas permeable material or has an array of microwells or both.

In various embodiments, the disclosure describes a nested permeable support device comprising a first well, a second well and a third well. The first well has a bottom, wherein at least a portion of the bottom is formed by a first porous membrane. The second well has a bottom, wherein at least a portion of the bottom is formed by a second porous membrane. A portion of either the first or the second permeable support may comprise an arcuate shape. The second well and the second permeable support are located below the first well and the first permeable support. The third well has a non-liquid permeable, gas permeable bottom which is located below the second well and the second permeable support.

In another embodiment, the disclosure describes a nested permeable support device comprising a first well, a second well, and a third well. The first well has a substrate forming a microwell array, the bottom of which is a porous membrane. The second well has a substrate forming a microwell array, the bottom of which is a porous membrane. The third well has a substrate forming a microwell array, the bottom of which is a non-liquid permeable, gas permeable support. The second well with the microwell array substrate with the porous membrane bottom is located beneath the first well with the microwell array substrate with the first porous membrane bottom and above the third well with the microwell array substrate with the non-liquid permeable, gas permeable bottom.

Additional features and advantages of the subject matter of the present disclosure will be set forth in the detailed description which follows, and in part will be readily apparent to those skilled in the art from that description or recognized by practicing the subject matter of the present disclosure as described herein, including the detailed description which follows, the claims, as well as the appended drawings.

It is to be understood that both the foregoing general description and the following detailed description present embodiments of the subject matter of the present disclosure, and are intended to provide an overview or framework for understanding the nature and character of the subject matter of the present disclosure as it is claimed. The accompanying drawings are included to provide a further understanding of the subject matter of the present disclosure, and are incorporated into and constitute a part of this specification. The drawings illustrate various embodiments of the subject matter of the present disclosure and together with the description serve to explain the principles and operations of the subject matter of the present disclosure. Additionally, the drawings and descriptions are meant to be merely illustrative, and are not intended to limit the scope of the claims in any manner.

BRIEF DESCRIPTION OF THE FIGURES

The following detailed description of specific embodiments of the present disclosure can be best understood when read in conjunction with the following drawings, where like structure is indicated with like reference numerals and in which.

DETAILED DESCRIPTION

Figure 1A:
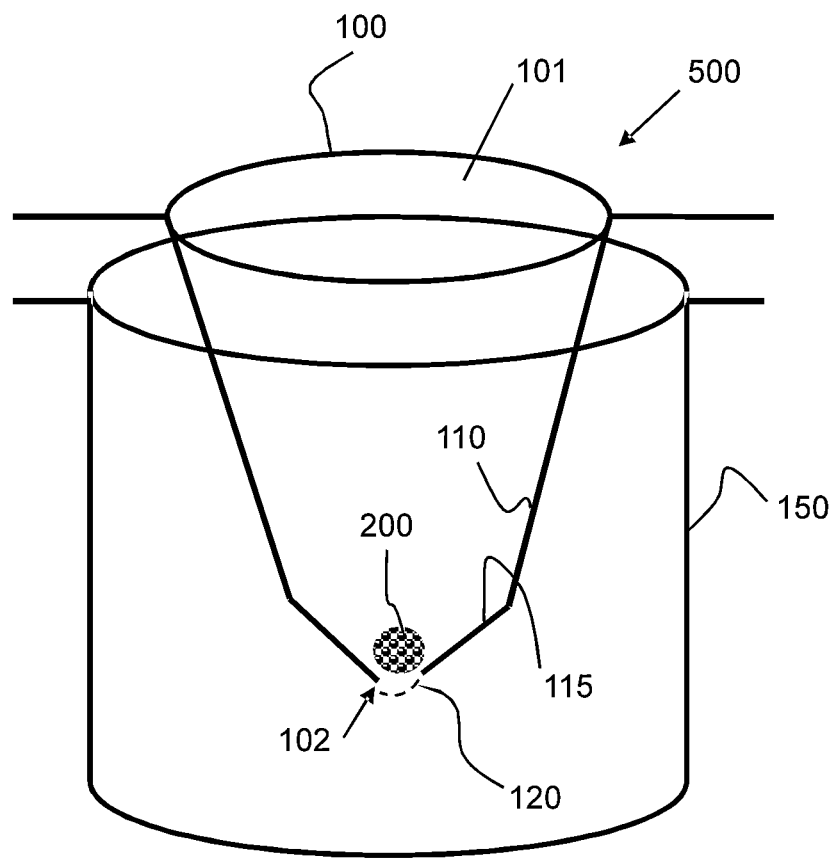
FIGS. 1A-C shows schematic diagrams of embodiments of cell culture inserts in which cells can be cultured to form a spheroid.

Reference will now be made in greater detail to various embodiments of the subject matter of the present disclosure, some embodiments of which are illustrated in the accompanying drawings. The same reference numerals will be used throughout the drawings to refer to the same or similar parts. However, it will be understood that the use of a number to refer to a component in a given figure is not intended to limit the component in another figure labeled with the same number. In addition, the use of different numbers to refer to components is not intended to indicate that the different numbered components cannot be the same or similar to other numbered components.

The present disclosure describes, among other things, spheroid-promoting cell culture inserts and methods of using spheroid-promoting cell culture inserts. In some embodiments, the spheroid-promoting cell culture inserts will be contained in a cell culture apparatus. In some embodiments, the spheroid-promoting cell culture inserts can be placed in another cell culture insert or another spheroid-promoting cell culture insert. In some embodiments, the spheroid-promoting cell culture insert can contain another cell culture insert or another spheroid-promoting cell culture insert. In various embodiments, a method of using spheroid-promoting cell culture inserts includes performing an experiment to test a New Chemical Entity (NCE) or a New Biological Entity (NBE).

Cell culture devices or apparatuses that include nested permeable support devices can be adapted to have a spheroid-promoting cell culture insert. Examples of such cell culture devices or apparatuses include TRANSWELL® Permeable Supports (Corning, Inc.), and MILLICELL® Cell Culture Inserts (EMD Millipore), as well as the cell culture articles and methods described in U.S. Pat. No. 8,163,537, which is incorporated herein by reference in its entirety to the extent that it does not conflict with the disclosure presented herein.

Figure 1B:
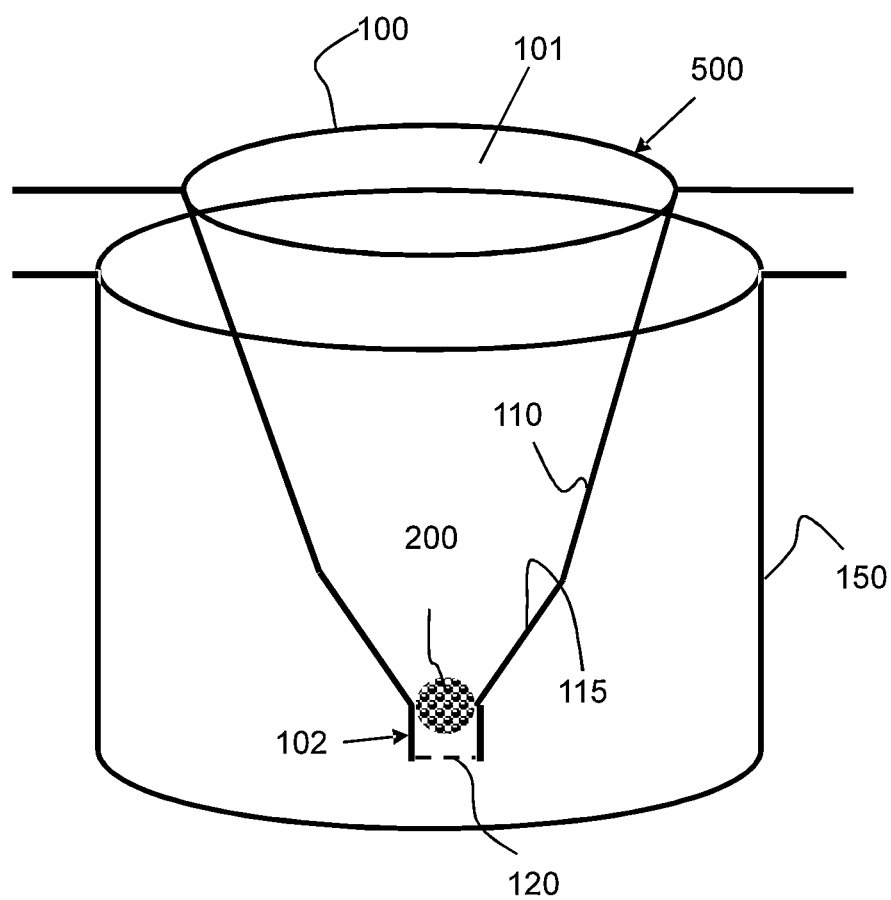
Figure 1C:
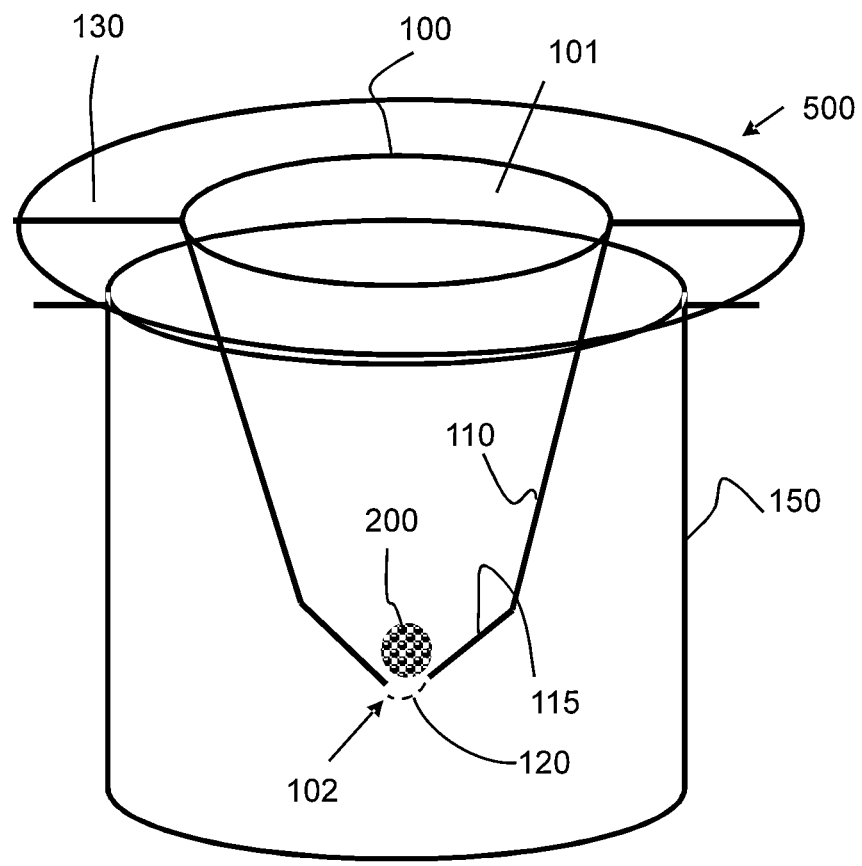

Referring now to FIGS. 1A-C, schematic side views of embodiments of cell culture apparatuses 500 are shown. The apparatuses 500 include spheroid-promoting cell culture inserts 100 that have one or more sidewalls 110 that are non-adherent to cells to cause the cells in the insert 100 to associate with each other and form spheroids 200. In embodiments, the insert fits inside a reservoir or a well 150 of a multiwell cell culture plate. In some embodiments, the one or more sidewalls 110 can be coated with an ultra-low binding material to make the wall non-adherent to cells. Examples of non-adherent material include perfluorinated polymers, olefins, or like polymers or mixtures thereof. Other examples include agarose, non-ionic hydrogels such as polyacrylamides, or polyethers such as polyethyleneoxide or polyols such as polyvinylalcohol or like materials or mixtures thereof.

The one or more sidewalls 110 of the spheroid-promoting cell culture inserts 100 include a portion that is sloped 115. In some embodiments, the one or more sidewalls can be sloped along their entire length. In other embodiments, only a portion of one or more sidewalls is sloped.

The one or more sidewalls 110 and other components of the spheroid-promoting cell culture inserts 100 can be formed of any suitable material. Preferably, materials intended to contact cells or culture media are compatible with the cells and the media. Typically, cell culture components are formed from polymeric material. Examples of suitable polymeric materials include polystyrene, polymethylmethacrylate, polyvinyl chloride, polycarbonate, polysulfone, polystyrene copolymers, fluoropolymers, polyesters, polyamides, polystyrene butadiene copolymers, fully hydrogenated styrenic polymers, polycarbonate PDMS copolymers, and polyolefins such as polyethylene, polypropylene, polymethyl pentene, polypropylene copolymers and cyclic olefin copolymers, and the like.

The spheroid-promoting cell culture insert 100 includes a body having a first open end 101 and a second end 102 wherein the end 102 defines an opening. A porous membrane 120 can cover the opening of the second end. In some embodiments, the porous membrane 120 can be adherent to cells. In other embodiments, the porous membrane 120, or a portion thereof, can be non-adherent to cells 200.

Figure 2A:
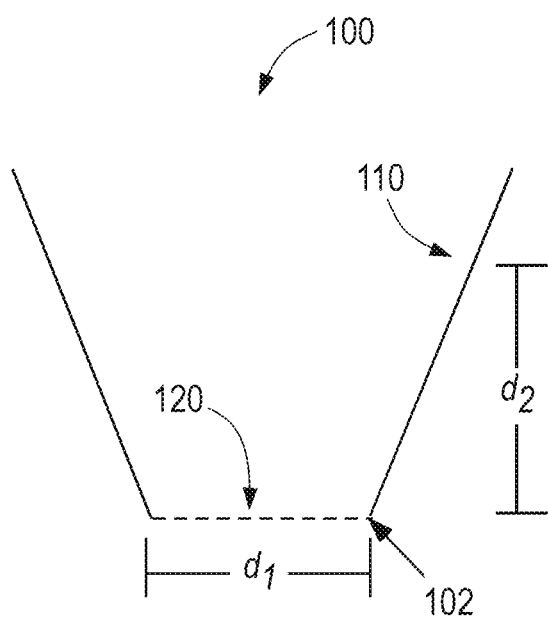
FIGS. 2A and 2B shows schematic diagrams of embodiments of a portion of a cell culture insert in which cells can be cultured to form a spheroid.
Figure 2B:
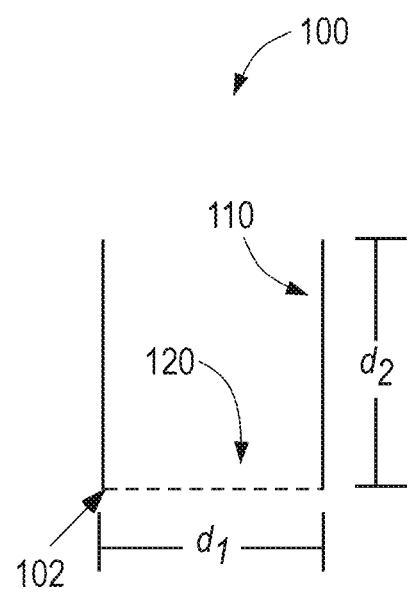

Referring now to FIG. 2A and FIG. 2B, the opening of the second end 102 of the body of the spheroid-promoting cell culture insert 100 can have a variety of shapes. In some embodiments, the opening forms a circle or an oval. In other embodiments, the opening defines a rectangle or other quadrilateral. In some embodiments, the opening of the second end has diametric dimension, such as a diameter, a width, a diagonal of a square or rectangle, or the like, $d_1$ in a range from 100 μm to 1000 μm. Specifically, the opening of the second end can have a diametric dimension $d_1$ of 100 μm, 150 μm, 200 μm, 250 μm, 300 μm, 350 μm, 400 μm, 450 μm, 500 μm, 550 μm, 600 μm, 650 μm, 700 μm, 750 μm, 800 μm, 850 μm, 900 μm, 950 μm, or 1000 μm, and any dimension encompassed within the range from 100 μm to 1000 μm.

The porous membrane 120 can have a variety of shapes. In some embodiments, the porous membrane 120 completely covers the opening of the second end of the body of the spheroid-promoting cell culture insert 100. In some embodiments the porous membrane can have an arcuate or curved shape. In some embodiments the second end of the body of the spheroid promoting cell culture insert is comprised of a microwell array with a porous membrane forming the bottom.

The porous membrane can be made of a variety of different materials including but not limited to track-etched membrane or a woven or non-woven porous material. The material of the porous membrane may be treated or coated to make it more adherent or more non-adherent to cells. Treatment may be accomplished by any number of methods known in the art which include plasma discharge, corona discharge, gas plasma discharge, ion bombardment, ionizing radiation, and high intensity UV light. Coatings can be introduced by any suitable method known in the art including printing, spraying, condensation, radiant energy, ionization techniques or dipping. The coatings may then provide either covalent or non-covalent attachment sites. Such sites can be used to attach moieties, such as cell culture components (e.g., proteins that facilitate growth or adhesion). Further, the coatings may also be used to enhance the attachment of cells (e.g., polylysine). Alternatively, cell non-adherent coatings as described above can be used to prevent or inhibit cell binding.

In embodiments, the porous membrane may be a substrate having an array of microwells.

In some embodiments, the spheroid formed by the cells 200 occludes the porous membrane 120 of the spheroid-promoting cell culture insert. (See for example, FIG. 1A). In some aspects, this occlusion prevents the passage of proteins, small molecules, and/or media from going around the spheroid.

The combination of, for example, non-adherent sidewalls, geometry, and gravity can define a confinement volume in which growth of cells cultured in the inserts is limited. In embodiments, this combination can promote the formation of spheroids by cells cultured in the inserts. The confinement volume can be defined by the portion of the one or more sidewalls proximate the second end and the width or diagonal of the second opening. In some embodiments, the portion of the one or more sidewalls proximate the second end $d_2$ is 500 µm, 450 µm, 400 µm, 350 µm, 300 µm, 250 µm, 200 µm, 150 µm, or 100 µm, or any length in between. In some embodiments the confinement volumes are defined by the wells of the microwell array substrate with the porous membrane that forms the bottom of the second opening. In which case, the second opening approximates the size of the first opening with the wells of the microwell array substrate comprising the confinement volume and have a diameter of $d_1$ 500 µm, 450 µm, 400 µm, 350 µm, 300 µm, 250 µm, 200 µm, 150 µm, or 100 µm, or any length in between.

Referring back to FIG. 1C, in some embodiments, the spheroid-promoting cell culture insert can further include a ledge 130 extending around the perimeter of the first open end where the ledge 130 is sized to support the spheroid-promoting cell culture insert 100 when it is positioned inside a reservoir 150. In some embodiments, at least a portion of the reservoir 150 is gas permeable.

As shown in FIG. 1A, a spheroid 200 can grow in a spheroid-promoting cell culture insert 100, a portion of which can include a porous membrane 120. One or both of the porous membrane 120 and the lower sidewalls 110 can be non-adherent to cells. The slope of the sidewall 110 encourages the seeded cells 200 to aggregate on the porous membrane 120. One or more of gravity, an ultra-low binding material, the sidewall geometry of the cell culture insert, and the arcuate shape of the porous membrane can facilitate the formation of a spheroid. In addition, in embodiments, the porous membrane may contain an array of microwells structured and arranged to form spheroids.

As shown in FIG. 1B, a spheroid can grow in a spheroid-promoting cell culture insert 100, a portion of which is a porous membrane 120. The porous membrane 120 and the lower sidewalls 110 can be non-adherent to cells. The slope of the sidewall 110 encourages the seeded cells to aggregate on or occlude the porous membrane 120. One or more of gravity, an ultra-low binding material, the sidewall geometry of the cell culture insert, and the cell confinement volume around the porous membrane 120 can facilitate the formation of a spheroid. The size of the spheroid can be limited by the confinement volume. In embodiments, the second end of the insert can have a shape that provides a confinement volume that promotes spheroid formation, a spheroid confinement volume.

Figure 3A:
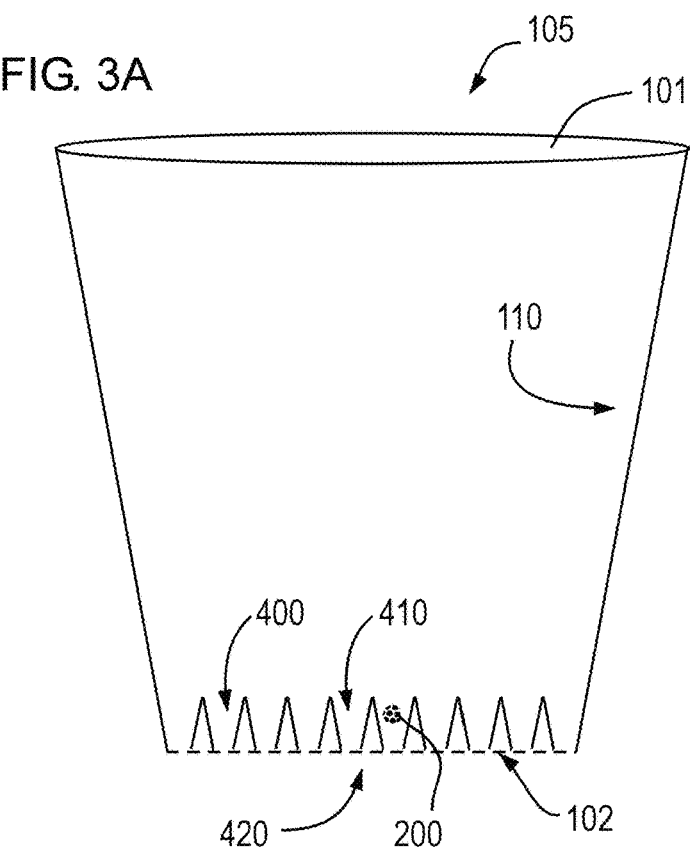
FIGS. 3A-D shows A, schematic diagram (side view) of embodiments of a cell culture insert in which cells can be cultured to form one or more spheroids; B, one embodiment of a substrate having an array of microwells at the second end of a cell culture insert; C, schematic diagram (top view) of the second end of a cell culture insert in which cells can be cultured to form one or more spheroids; D, schematic diagram (enlarged side view) of an array of microwells on a substrate with a bottom having a porous membrane forming the second end of a cell culture insert in which cells can be cultured to form one or more spheroids.

As shown in FIG. 3A, in some embodiments, a spheroid-promoting cell culture insert 105 can have a first open end 101 and a second end, 102 and one or more sidewalls 110 extending from the first open end to the second end. In some embodiments, the sidewalls are sloped. In one aspect, the second end of the spheroid-promoting cell culture insert 105 contains multiple spheroid-promoting wells 400, where each spheroid-promoting well may have a sidewall 410. In some embodiments, the spheroid-promoting cell culture insert 105 can have one or more sidewalls 110 that are non-adherent to cells.

Figure 3B:
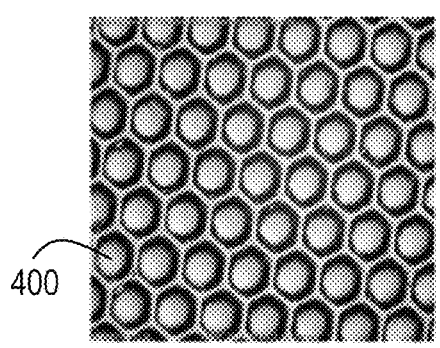
Figure 3C:
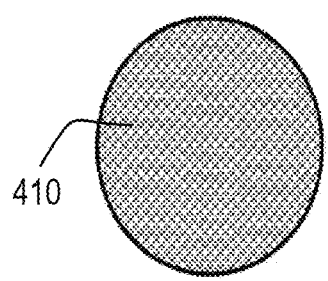

In some embodiments, the substrate having an array of microwells is comprised of hexagonal close-packed well structures. An image of an embodiment of such a substrate having an array of microwells 410 is shown in FIG. 3B, showing the hexagonally shaped wells 400. FIG. 3C is a schematic drawing showing a top-down view of an embodiment of a substrate having an array of microwells 410. In some preferred embodiments, cells cultured within each well 400 form a single spheroid 200.

Figure 3D:
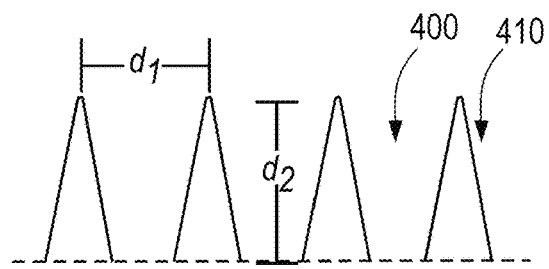

As shown in FIG. 3D, in some embodiments, the wells 400 of the spheroid-promoting cell culture insert 105 have an inner surface that defines an upper aperture and a nadir, or low point or surface. At the upper aperture the wells have a diametric dimension, such as a diameter, a width, a diagonal of a square or rectangle, or the like, $d_3$, in a range from 100 µm to 1000 µm. Specifically, the well can have a diametric dimension $d_3$ of 100 µm, 150 µm, 200 µm, 250 µm, 300 µm, 350 µm, 400 µm, 450 µm, 500 µm, 550 µm, 600 µm, 650 µm, 700 µm, 750 µm, 800 µm, 850 µm, 900 µm, 950 µm, or 1000 µm, and any dimension encompassed within the range from 100 µm to 1000 µm. In some embodiments, the depth of the wells 400 $d_4$ is 1000 µm, 500 µm, 450 µm, 400 µm, 350 µm, 300 µm, 250 µm, 200 µm, 150 µm, or 100 µm, or any dimension encompassed within the range from 100 µm to 1000 µm.

In some embodiments, a substrate having an array of microwells with a porous support forming the bottom of the microwells 410 covers the second end of the spheroid-promoting cell culture insert 105. In some embodiments, at least a portion of the substrate having an array of microwells 410 is non-adherent to cells. In some embodiments, at least a portion of the substrate having an array of microwells 410 is adherent to cells. In some embodiments, a portion of the substrate having an array of microwells 410 is porous. In further embodiments, a portion of the substrate having an array of microwells 410 forming the wells 400 includes openings. In some embodiments, the substrate having an array of microwells 410 can be adhered to, affixed to, or juxtaposed with a porous membrane 420. In one embodiment, the second end of the spheroid-promoting cell culture insert 105 is covered by a porous membrane 420, and the porous membrane defines the substrate having an array of microwells 410.

In some embodiments, at least a portion of the substrate having an array of microwells 410 forming the wells 400 of the spheroid-promoting cell culture insert 105 are sloped. In some embodiments, the substrate having an array of microwells 410 forming the wells 400 can be sloped along the entire depth of the well.

A structured bottom surface as described herein can be formed in any suitable manner. For example, a substrate can be coined, injection molded or embossed to form the substrate having an array of microwells 410. A porous material or a gas permeable material can be coined, injection molded or embossed to form a substrate having an array of microwells.

Figures 4A, 4B:
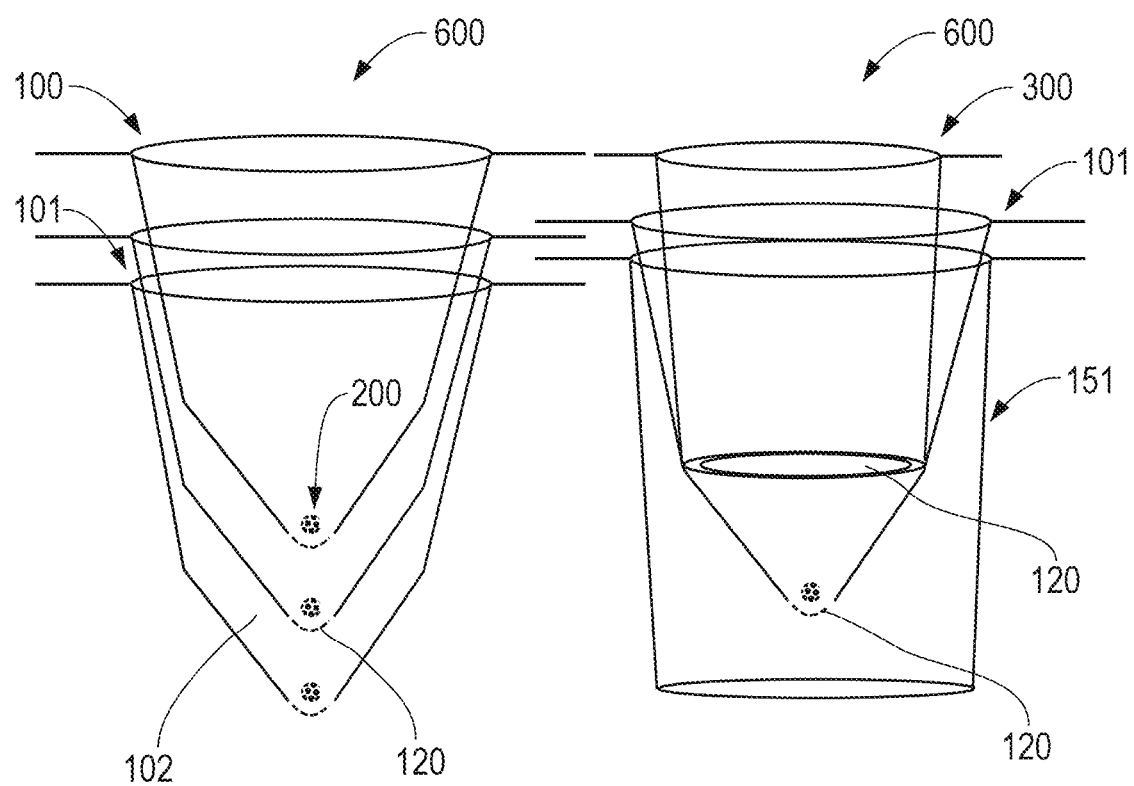
FIGS. 4A-B shows schematic diagrams of some embodiments of nested cell culture inserts in which cells can be cultured to form one or more spheroids.

Referring now to FIGS. 4A-B, in some embodiments, a spheroid-promoting cell culture insert 100 can be used in a nested permeable support device 600. In some embodiments, a spheroid-promoting cell culture insert 100 can be placed in another cell culture insert or device or another spheroid-promoting cell culture insert. In one aspect two, or three, or more spheroid-promoting cell culture inserts 100 can be nested. In another aspect, a spheroid-promoting cell culture insert 100 can be placed in another cell culture insert or can have another cell culture insert placed in it. In some embodiments, the spheroid-promoting cell culture insert can further include a ledge extending around the perimeter of the first open end where the ledge is sized to support the spheroid-promoting cell culture insert when it is positioned inside a reservoir or another cell culture insert. One having ordinary skill in the art of cell culture would recognize that any combination of spheroid-promoting cell culture inserts and other cell culture inserts could be constructed. Each cell culture insert can have a porous membrane 120 or can be gas permeable. In one embodiment, the lowest cell culture insert or reservoir is gas-permeable and the upper cell inserts have porous membranes 120.

For example, as shown in FIG. 4A, a nested device can include an upper 100 and a middle 101 spheroid-promoting cell culture insert. The upper 100 and middle 101 spheroid-promoting cell culture inserts can have a porous membrane 120 at the nadir. In embodiments, the porous membrane is a substrate having an array of microwells. The nested device can further include a spheroid-promoting cell culture reservoir 102 that does not have a permeable support. In some embodiments, the spheroid-promoting cell culture reservoir 102 can be made of or include a portion of a gas-permeable material. In embodiments the gas permeable material is a substrate having an array of microwells.

As shown in the embodiment shown is FIG. 4B, only the middle cell culture insert 101 can be a spheroid-promoting cell culture insert, but both the uppermost cell culture insert 300 and middle spheroid-promoting cell culture insert 101 have porous membranes 120. The lowest device can be a reservoir 151. In one embodiment, the reservoir 151 can be gas-permeable.

Figures 5A, 5B:
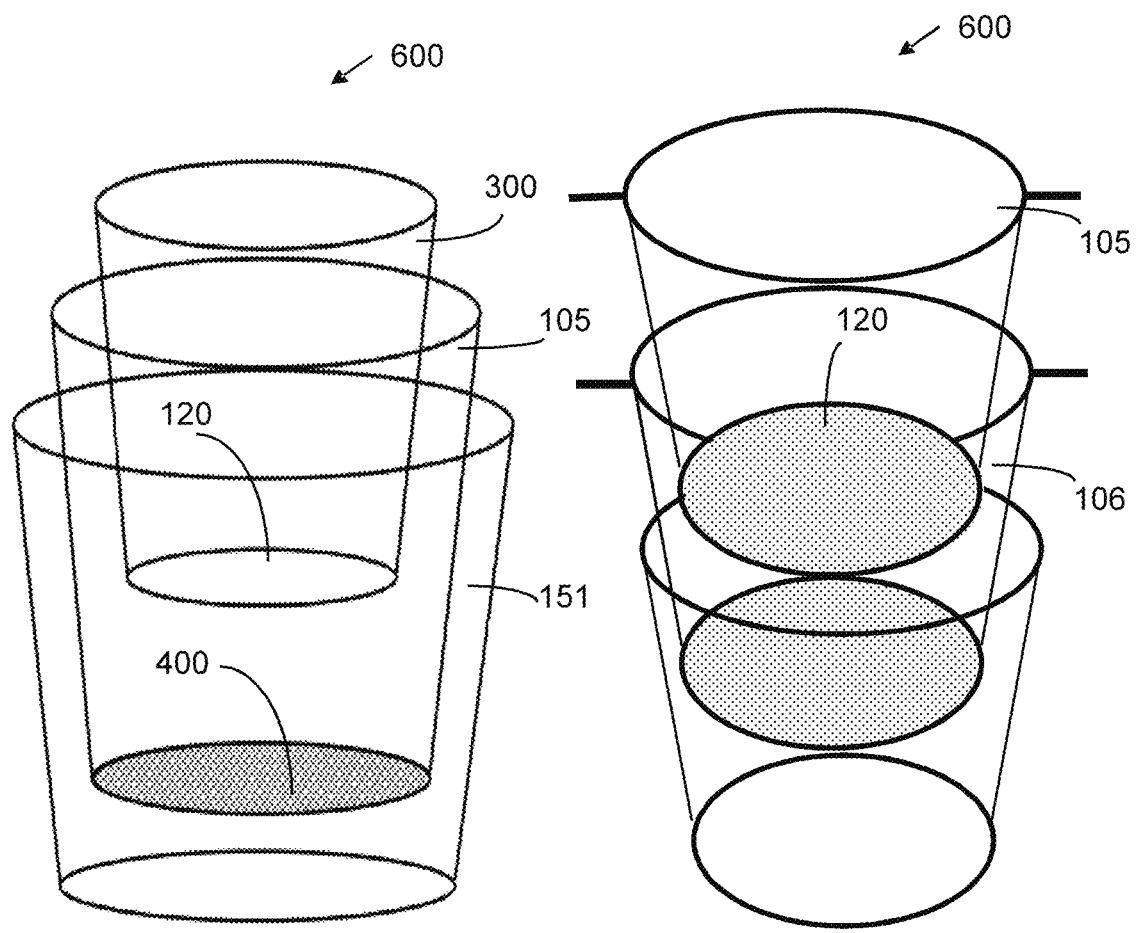
FIG. 5A-B shows schematic diagrams of some embodiments of nested cell culture inserts in which cells can be cultured to form one or more spheroids on any or all of the cell culture substrates forming the well bottoms.

As shown in FIG. 5A, the middle cell culture insert can be a spheroid-promoting cell culture insert 105 that contains multiple spheroid-promoting porous wells 400. The uppermost cell culture insert 300 can have a porous membrane 120. The spheroid-promoting cell culture insert 105 can be inserted in or nested in a reservoir 151. In one embodiment, the reservoir 151 can be gas-permeable. Using a spheroid-promoting cell culture insert 105 that contains multiple spheroid-promoting wells 400 permits tighter nesting with flat bottomed inserts that culture 2D cell sheets (such as those depicted in FIGS. 4A&B and would also provide more spheroids for amplifying signal and the cell processing rate, preventing bottlenecks in a testing system. FIG. 5B shows an embodiment of an apparatus with first 105 and second 106 spheroid-promoting cell culture inserts having porous membrane bottoms 120 in a spheroid-promoting reservoir 151 having a non-liquid permeable, gas permeable bottom. In addition to providing greater signal amplification the more physiologic functionality of the spheroids can better approximate a replacement for animal testing. As will be understood by those of ordinary skill in the art, any combination of cell culture supports, each having porous membranes or not, having substrates having an array of microwells for spheroid promotion or not, or being gas permeable or not, are possible depending on the desired cell culture environment.

In some embodiments, the spheroid-promoting cell culture inserts can be used in a method to determine whether a compound or molecule known as a NCE has a desired biological activity. Such methods are described in, for example, U.S. Pat. No. 8,163,537. These methods often entail examining the Absorption, Distribution, Metabolism, Excretion, and Toxicity (ADME-Tox) of the NCE, as well as determining the NCE's level of effectiveness for the targeted therapeutic indication including pharmacokinetic parameters. One type of assessment examines the "first pass effect." This assessment involves experimental determination of the bioavailabilty of the NCE following its absorption through the digestive tract and then its metabolism by the liver. Commonly, the assessment of the "first pass effect" requires two separate in vitro assays to be conducted, and the data combined, to determine the intestinal permeability and the hepatic metabolism. If desired, additional studies may be conducted to determine target selectivity, efficacy and dosage (Lau et al., Drug Metabolism and Disposition, Vol. 32, No. 9, pp. 937-942, 2004).

A well-known method used today to examine the intestinal absorption of a NCE is known as the Caco 2 cell-based assay which is typically conducted on permeable supports such as the ones sold under the brand name of Transwell™ and manufactured by Corning Inc. ("Transwell® Permeable Supports: Including Snapwell™ and Netwell™ Inserts—Instructions for Use" Corning Inc., September 2007.) The design of the Transwell™ permeable support facilitates the development of Caco 2 cell polarization to create more in vivo-like test conditions. Researchers from the Schering-Plough Research Institute have expanded the utility of the Caco 2 cell-based assay by adding hepatocytes in the nutrient medium to a Transwell™ receiver plate which receives the Transwell™ permeable support. In this way, the researchers were able to more accurately predict the oral bioavailability of NCE's. However, the hepatic cell viability under these conditions during a 3 hour incubation period was only 50-70%, limiting the potential of this method (Lau et al., Drug Metabolism and Disposition, Vol. 32, No. 9, pp. 937-942, 2004). Another group of researchers from the University of Tokyo co-cultured Caco-2 cells on the Transwell™ permeable support with monolayers of Hep G2 cells growing on the inner surface of the Transwell™ receiver plate. While useful for some assays, the Hep G2 cells did not maintain the functions that are representative of in vivo hepatocytes (Choi et al., Toxicology in Vitro, vol. 18, pages 393-402, 2004).

The current United States Food and Drug Administration Guidance regarding drug interaction studies like the first pass assay recommends the use of in vitro assays with fresh or cryopreserved human hepatocytes due to species specific responses. (U.S. Department of Health and Human Services et al. "Guidance for Industry: Drug Interaction Studies-Study, Design, Data Analysis, and Implications for Dosing and Labeling", Clinical Pharmacology, September 2006.) However, it is well known that primary hepatocytes loose differentiated function rapidly in standard cell culture conditions on tissue culture treated polystyrene. The loss of normal differentiated hepatocyte function decreases the in vivo-like conditions and hence also decreases the relevance of experimental data in ADME-Tox and pharmacokinetic in vitro assays.

In some embodiments of the methods described herein, hepatocytes or Hep G2 cells used in a Caco 2 cell-based assay are cultured in a spheroid-promoting cell culture insert.

In some embodiments, the present disclosure relates to a nested permeable support device and methods for using the nested permeable support device to perform various experiments to test new therapeutic compounds, NBEs, or NCEs.

In some embodiments, the spheroid-promoting cell culture inserts can be used to assess system-like communication information. In some embodiments, the spheroid-promoting cell culture inserts can be used to create cell models that represent a series of human organs in vertical orientation.

In one aspect, the nested permeable support device is used to form a first pass assay to determine the bioavailability of a NCE or NBE following absorption from the digestive tract and metabolism by the liver.

In one embodiment, the nested permeable support device 600 can be used to perform a first pass assay to determine the bioavailability of a NCE following absorption through the digestive tract and metabolism by the liver. In another embodiment, the nested permeable support device 600 can be used to perform a first pass assay to determine the bioavailability of a NBE following absorption through the digestive tract and metabolism by the liver.

For instance, a researcher using the embodiment shown in FIG. 5A can place a media in a growing reservoir and then place the upper insert 300 in the growing reservoir. The upper insert 300 is then filled with a volume of Caco 2 cells in media. The upper insert 300 and growing reservoir are in communication until a confluent monolayer of Caco 2 cells is formed across the permeable support of the upper insert 300. It usually takes about a month for Caco 2 cells to form across the permeable support of the upper insert 300. The Caco 2 cells can be tested electronically to determine how tightly the Caco 2 cells adhere to one another by performing a Trans Epithelial Electrical Resistance (TEER) test, where a probe is inserted into the upper insert 300 and then the probe initiates a pulse that is detected by another probe located in the growing reservoir below the permeable support. Another test that can be performed uses a dye called Lucifer yellow, which can pass through gaps in the Caco 2 cell monolayer. The more Lucifer yellow that shows up in the growing reservoir after being introduced in the upper insert 300, the less mature (or confluent) the monolayer of Caco 2 cells. Tests such as these can be performed to make sure the Caco 2 cell culture is functioning as expected.

In parallel, the researcher can place a media in another growing reservoir and then place the middle insert 105 in this growing reservoir. The middle insert 105 is then filled with a volume of hepatocytes in media. The middle insert 105 and reservoir are in communication until a spheroid of hepatocytes is formed across the second permeable support. Tests could also be conducted to assure that the hepatocytes are functioning appropriately. Alternatively, the upper insert 300 and middle insert 105 can be placed in a reservoir 151 to grow the Caco 2 cells and the hepatocytes.

Once the Caco 2 cells and the hepatocytes have been cultured, the upper and middle inserts 300 and 105 would be lifted out of their respective growing reservoirs. The middle insert 105 would be placed (nested) in the reservoir 151 which contains a media. Some media would then be placed above the layer of hepatocytes located within the middle insert 105. Then, the upper insert 300 would be placed (nested) in the middle insert 105. The NCE/NBE and media would be dispensed above the layer of Caco 2 cells located within the upper insert 300. After a period of incubation, the upper insert 300 could be removed and the media in the middle insert 105 could be tested (i.e., LS/MS) to determine if the NCE/NBE passed through the intestinal epithelium (Caco 2 cells). If the NCE/NBE did pass through the Caco 2 cells, then the middle insert 105 could be removed and the media in the reservoir 151 could be tested (i.e., LC/MS) to check the bioavailability of the NCE and/or how the NCE/NBE is metabolized by the liver (hepatocytes) to form metabolic products. The hepatocytes could also show if the NCE/NBE is toxic at the dosage applied. If there are target cells (or molecules) on the bottom of the reservoir 151, then these could be examined (i.e., LC/MS) to determine the drug effects either microscopically, or by using an assay that is separate from the Caco 2 cells and hepatocytes by pulling out the inserts 300 and 105. Alternatively, the target cells (or molecules) on the bottom of the reservoir 151 could be examined using an interrogation system to assess function and viability as described, for example, in U.S. Pat. No. 8,163,537. An assay such as this will enable understanding of whether 1) an NCE/NBE can pass through the intestinal epithelium; 2) whether the liver metabolizes or is damaged by an NCE/NBE; and 3) the effect on the target cells of unmodified or liver-metabolized NCE/NBE.

In another embodiment, the nested permeable support device 100 can be used to test a NCE which would not pass through the digestive tract but instead would enter the body via inhalation in which case the Caco 2 cells would be replaced with nasal mucosal cells, bronchial cells or lung epithelial cells, etc. In practice, the researcher would typically select the actual cells used in the nested permeable support device 600.

In some embodiments, particularly where multiple wells are provided on a second end or where nested supports are employed, multiple spheroids may be grown. In some embodiments, the spheroids are all the same. In other embodiments, two or more different types of spheroids are used (e.g., a co-culture system to, for example, simulate or reconstitute the multicellular functionality of an organ). Where cells are imaged or signal generated from the cells is detected, the response from multiple cells may simultaneously be analyzed or the results from individual cells or groups of cells pooled, as desired.

Cells cultured in three dimensions, such as spheroids, can exhibit more in vivo like functionality than their counterparts cultured in two dimensions as monolayers. In two dimensional cell culture systems, cells can attach to a substrate on which they are cultured. However, when cells are grown in three dimensions, such as spheroids, the cells interact with each other rather than attaching to the substrate. Cells cultured in three dimensions more closely resemble in vivo tissue in terms of cellular communication and the development of extracellular matrices. Spheroids thus provide a superior model for cell migration, differentiation, survival, and growth and therefore provide better systems for research, diagnostics, and drug efficacy, pharmacology, and toxicity testing.

In some embodiments, the devices are configured such that cells cultured in the devices form spheroids. For example, the wells in which cells are grown can be non-adherent to cells to cause the cells in the wells to associate with each other and form spheres. The spheroids expand to size limits imposed by the geometry of the wells. In some embodiments, the wells are coated with an ultra-low binding material to make the wells non-adherent to cells.

Examples of non-adherent material include perfluorinated polymers, olefins, or like polymers or mixtures thereof. Other examples include agarose, non-ionic hydrogels such as polyacrylamides, polyethers such as polyethylene oxide and polyols such as polyvinyl alcohol, or like materials or mixtures thereof. The combination of, for example, non-adherent wells, well geometry (e.g., size and shape), and/or gravity induce cells cultured in the wells to self-assemble into spheroids. Some spheroids maintain differentiated cell function indicative of a more in vivo-like, response relative to cells grown in a monolayer. Other cells types, such as mesenchymal stromal cells, when cultured as spheroids retain their pluripotency.

In some embodiments, the systems, devices, and methods herein comprise one or more cells. In some embodiments, the cells are cryopreserved. In some embodiments, the cells are in three dimensional culture. In some such embodiments, the systems, devices, and methods comprise one or more spheroids. In some embodiments, one or more of the cells are actively dividing. In some embodiments, the systems, devices, and methods comprise culture media (e.g., comprising nutrients (e.g., proteins, peptides, amino acids), energy (e.g., carbohydrates), essential metals and minerals (e.g., calcium, magnesium, iron, phosphates, sulphates), buffering agents (e.g., phosphates, acetates), indicators for pH change (e.g., phenol red, bromo-cresol purple), selective agents (e.g., chemicals, antimicrobial agents), etc.). In some embodiments, one or more test compounds (e.g., drug) are included in the systems, devices, and methods.

A wide variety of cell types may be cultured. In some embodiments, a spheroid contains a single cell type. In some embodiments, a spheroid contains more than one cell type. In some embodiments, where more than one spheroid is grown, each spheroid is of the same type, while in other embodiments, two or more different types of spheroids are grown. Cells grown in spheroids may be natural cells or altered cells (e.g., cell comprising one or more non-natural genetic alterations). In some embodiments, the cell is a somatic cell. In some embodiments, the cell is a stem cell or progenitor cell (e.g., embryonic stem cell, induced pluripotent stem cell) in any desired state of differentiation (e.g., pluripotent, multi-potent, fate determined, immortalized, etc.). In some embodiments, the cell is a disease cell or disease model cell. For example, in some embodiments, the spheroid comprises one or more types of cancer cells or cells that can be induced into a hyper-proliferative state (e.g., transformed cells). Cells may be from or derived from any desired tissue or organ type, including but not limited to, adrenal, bladder, blood vessel, bone, bone marrow, brain, cartilage, cervical, corneal, endometrial, esophageal, gastrointestinal, immune system (e.g., T lymphocytes, B lymphocytes, leukocytes, macrophages, and dendritic cells), liver, lung, lymphatic, muscle (e.g., cardiac muscle), neural, ovarian, pancreatic (e.g., islet cells), pituitary, prostate, renal, salivary, skin, tendon, testicular, and thyroid. In some embodiments, the cells are mammalian cells (e.g., human, mice, rat, rabbit, dog, cat, cow, pig, chicken, goat, horse, etc.).

The cultured cells find use in a wide variety of research, diagnostic, drug screening and testing, therapeutic, and industrial applications.

In some embodiments, the cells are used for production of proteins or viruses. Systems, devices, and methods that culture large numbers of spheroids in parallel are particularly effective for protein production. Three-dimensional culture allows for increased cell density, and higher protein yield per square centimeter of cell growth surface area. Any desired protein or viruses for vaccine production may be grown in the cells and isolated or purified for use as desired. In some embodiments, the protein is a native protein to the cells. In some embodiments, the protein is non-native. In some embodiments, the protein is expressed recombinantly. Preferably, the protein is overexpressed using a non-native promoter. The protein may be expressed as a fusion protein. In some embodiments, a purification or detection tag is expressed as a fusion partner to a protein of interest to facilitate its purification and/or detection. In some embodiments, fusions are expressed with a cleavable linker to allow separation of the fusion partners after purification.

In some embodiments, the protein is a therapeutic protein. Such proteins include, but are not limited to, proteins and peptides that replace a protein that is deficient or abnormal (e.g., insulin), augment an existing pathway (e.g., inhibitors or agonists), provide a novel function or activity, interfere with a molecule or organism, or deliver other compounds or proteins (e.g., radionuclides, cytotoxic drugs, effector proteins, etc.). In some embodiments, the protein is an immunoglobulin such as an antibody (e.g., monoclonal antibody) of any type (e.g., humanized, bi-specific, multi-specific, etc.). Therapeutic protein categories include, but are not limited to, antibody-based drugs, Fc fusion proteins, anticoagulants, antigens, blood factor, bone morphogenetic proteins, engineered protein scaffolds, enzymes, growth factors, hormones, interferons, interleukins, and thrombolytics. Therapeutic proteins may be used to prevent or treat cancers, immune disorders, metabolic disorders, inherited genetic disorders, infections, and other diseases and conditions.

In some embodiments, the protein is a diagnostic protein. Diagnostic proteins include, but are not limited to, antibodies, affinity binding partners (e.g., receptor-binding ligands), inhibitors, antagonists, and the like. In some embodiments, the diagnostic protein is expressed with or is a detectable moiety (e.g., fluorescent moiety, luminescent moiety (e.g., luciferase), colorimetric moiety, etc.).

In some embodiments, the protein is an industrial protein. Industrial proteins include, but are not limited to, food components, industrial enzymes, agricultural proteins, analytical enzymes, etc.

In some embodiments, the cells are used drug discovery, characterization, efficacy testing, and toxicity testing. Such testing includes, but is not limited to, pharmacological effect assessment, carcinogenicity assessment, medical imaging agent characteristic assessment, half-life assessment, radiation safety assessment, genotoxicity testing, immunotoxicity testing, reproductive and developmental testing, drug interaction assessment, dose assessment, adsorption assessment, disposition assessment, metabolism assessment, elimination studies, etc. Specific cells types may be employed for specific tests (e.g., hepatocytes for liver toxicity, renal proximal tubule epithelial cells for nephrotoxicity, vascular endothelial cells for vascular toxicity, neuronal and glial cells for neurotoxicity, cardiomyocytes for cardiotoxicity, skeletal myocytes for rhabdomyolysis, etc.). Treated cells may be assessed for any number of desired parameters including, but not limited to, membrane integrity, cellular metabolite content, mitochondrial functions, lysosomal functions, apoptosis, genetic alterations, gene expression differences, and the like.

In some embodiments, the cell culture devices are a component of a larger system. In some embodiments, the system comprises a plurality (e.g., 2, 3, 4, 5, . . . , 10, . . . , 20, . . . , 50, . . . , 100, . . . , 1000, etc.) of such cell culture devices. In some embodiments, the system comprises an incubator for maintaining the culture devices at optimal culture conditions (e.g., temperature, atmosphere, humidity, etc.). In some embodiments, the system comprises detectors for imaging or otherwise analyzing cells. Such detectors include, but are not limited to, fluorimeters, luminometers, cameras, microscopes, plate readers (e.g., PERKIN ELMER ENVISION plate reader; PERKIN ELMER VIEWLUX plate reader), cell analyzers (e.g., GE IN Cell Analyzer 2000 and 2200; THERMO/CELLOMICS CELLNSIGHT High Content Screening Platform), and confocal imaging systems (e.g., PERKIN ELMER OPERA-PHENIX high throughput content screening system; GE INCELL 6000 Cell Imaging System). In some embodiments, the system comprises perfusion systems or other components for supplying, re-supplying, and circulating culture media or other components to cultured cells. In some embodiments, the system comprises robotic components (e.g., pipettes, arms, plate movers, etc.) for automating the handing, use, and/or analysis of culture devices.

A number of aspects of inserts, methods and assemblies have been disclosed herein. A summary of some selected aspects is presented below. In a first aspect, a cell culture insert comprises (i) a body having a first open end, a second end wherein the second end defines an opening having a diametric dimension in a range from 100 µm to 1000 µm, and one or more sidewalls extending from the first open end to the second end; wherein the one or more sidewalls are sloped; and (ii) a porous membrane disposed over the opening of the second end.

A second aspect is a cell culture insert according the first aspect wherein at least a portion of the one or more sidewalls are non-adherent to cells.

A third aspect is a cell culture insert according to aspect 1 or aspect 2, wherein at least a portion of the porous membrane is non-adherent to cells.

A fourth aspect is a cell culture insert according to any one of aspects 1 to 3, wherein at least a portion of the porous membrane is adherent to cells.

A fifth aspect is a cell culture insert according to any one of aspects 1 to 4, wherein a portion of the one or more sidewalls proximate the second end at least partially define a cell confinement volume.

A sixth aspect is a cell culture insert according to aspect 5 wherein a depth of the confinement volume is in a range from 100 µm to 1000 µm.

A seventh aspect is a cell culture insert according to any one of aspects 1 to 6, wherein the insert is configured such that cells cultured in the insert form a spheroid.

An eighth aspect is a method for culturing a spheroid comprising (i) placing cell culture insert according to aspect 7 in a reservoir, the reservoir having a bottom, wherein insert is placed in the reservoir such that the second end of body of the insert is positioned above the bottom of the insert; (ii) introducing cells into the insert; (iii) introducing a cell culture medium into the insert; and (iv) culturing the cells in the cell culture medium in the insert to form the spheroid.

A ninth aspect is a cell culture assembly, comprising (i) a reservoir defining an interior and having a bottom; and (ii) a first cell culture insert according to any one of aspects 1 to 7 configured to be positioned in the interior of the reservoir such that the second end of the body is above the bottom or the reservoir, wherein the body of the first insert defines an interior of the first insert.

A tenth aspect is a cell culture assembly according to aspect 9, wherein the interior of the first insert, when the first insert is positioned in the interior of the reservoir, is in fluid communication with the interior of the reservoir only through the porous membrane disposed over the opening of the second end of the body of the first insert.

An eleventh aspect is a cell culture assembly according to aspect 9 or aspect 10, further comprising a second insert having a body defining an interior, the body comprising a first open end, a second end defining an opening, and one or more sidewalls extending from the first open end to the second end, wherein the second insert is configured to be positioned in the interior of the first insert such that the second end of the body of the second insert above the second end of the body of the first insert.

A twelfth aspect is a cell culture assembly according to aspect 11, wherein the interior of the second insert, when the second insert is positioned in the interior of the first insert, is in fluid communication with the interior of the first insert only through the porous membrane disposed over the opening of the second end of the body of the second insert.

A thirteenth aspect is a method comprising (i) introducing target cells and a cell culture medium to an interior of a reservoir of a cell culture assembly according to aspect 12 such that the target cells grow on the bottom of the reservoir; (ii) positioning a first cell culture insert according to aspect 12 in the interior of the reservoir; (iii) introducing a plurality of a first type of cells and a cell culture medium into the interior of the first cell culture insert such that cells of the first type grow as a spheroid in proximity to the porous membrane of the first insert; (iv) positioning a second cell culture insert according to aspect 12 in the interior of the first insert; and (v) introducing a plurality of a second type of cells and a cell culture medium into the interior of the second cell culture insert such that the cells of the second type grow in proximity to the porous membrane of the second insert.

A fourteenth aspect is a method according to aspect 13, wherein the cells of the second type cover the porous membrane of the second insert such that compounds or metabolic derivatives thereof that move from the interior of the second insert to the interior of the first insert pass through the cells of the second type.

A fifteenth aspect is a method according to aspect 14, wherein the cells of the first type attach to the porous membrane of the first insert such that compounds or metabolic derivatives thereof that move from the interior of the first insert to the interior of the reservoir pass through the cells of the first type.

A sixteenth aspect is a method according to aspect 15, further comprising: (i) introducing a test compound to the interior of the second insert; and (ii) identifying an effect of the test compound or a metabolic derivative thereof on the target cells.

A seventeenth aspect is a method according to any of aspects 13 to 16, wherein the cells of the first type are hepatocytes.

An eighteenth aspect is a method according to any of aspects 13 to 17, wherein the cells of the second type are Caco 2 cells.

A nineteenth aspect is a cell culture insert comprising: (i) a body having a first open end, a second end wherein the second end defines an opening, and one or more sidewalls extending from the first open end to the second end; wherein the one or more sidewalls are sloped; and (ii) a porous membrane disposed over the opening of the second end, wherein the porous membrane is non-adherent to cells.

A twentieth aspect is a permeable support device configured to be at least partially inserted into a reservoir of a cell culture device, the permeable support device comprising a first well having a tapered shape and bottom at least partially defined by a first permeable support.

A twenty-first aspect is a permeable support device of aspect 20 wherein the well is configured such that cells cultured in the well form a spheroid.

A twenty-second aspect is a permeable support device of either of aspects 20 or 21 wherein at least a portion of the first well is coated with an ultra-low binding material.

A twenty-third aspect is a permeable support device of any of aspect 20 to 22, wherein at least a portion of the permeable support is configured to attach to cells cultured in the first well.

A twenty-fourth aspect is a permeable support device of any of aspects 20 to 23 wherein at least a portion of the first well comprises an arcuate shape A twenty-fifth aspect is a permeable support device of any of aspects 20 to 24 wherein at least a portion of the first well comprises a conical shape.

A twenty-sixth aspect is a permeable support device of any of aspects 20 to 25 wherein a portion of the well defines a confinement volume.

A twenty-seventh aspect is a permeable support device of aspect 26 wherein a diametric dimension of the confinement volume is in a range from 200 μm to 500 μm.

A twenty-eighth aspect The permeable support device of either of aspects 26 or 27 wherein the depth of the confinement volume is in a range from 100 μm to 500 μm.

A twenty-ninth aspect is a permeable support device of aspect any of aspects 20 to 28 wherein the first well is configured and sized to receive a second well having a bottom, wherein the second well is located above the first well.

A thirtieth aspect is a nested permeable support device comprising: (i) a first well having a tapered shape and a bottom portion at least partially defined by a first permeable support; and (ii) a reservoir having a bottom located below the first well.

A thirty-first aspect is a nested permeable support device of aspect 30 wherein the well is configured such that cells cultured in the well form a spheroid.

A thirty-second aspect is a nested permeable support device of either of aspects 30 or 31 wherein at least a portion of the first well is coated with an ultra-low binding material.

A thirty-third aspect is a nested permeable support device of any of aspects 29 to 32, wherein at least a portion of the permeable support is configured to attach to cells cultured in the first well.

A thirty-fourth aspect is a nested permeable support device of any of aspects 30 to 33 wherein at least a portion of the first well comprises an arcuate shape.

A thirty-fifth aspect is a nested permeable support device of any of aspects 30 to 34 wherein at least a portion of the first well comprises a conical shape.

A thirty-sixth aspect is a nested permeable support device of any of aspects 30 to 35 wherein a portion of the well defines a confinement volume.

A thirty-seventh aspect is a nested permeable support device of aspect 36 wherein a diametric dimension of the confinement volume is in a range from 100 μm to 1000 μm, e.g., 100, 150, 200, 250, 300, 350, 400, 450, 500, 550, 600, 650, 700, 750, 800, 850, 900, 950, or 1000 μm, including ranges between any of the foregoing.

A thirty eighth aspect is a nested permeable support device of either of aspects 36 or 37 wherein the depth of the confinement volume is in a range from 100 μm to 1000 μm, e.g., 100, 150, 200, 250, 300, 350, 400, 450, 500, 550, 600, 650, 700, 750, 800, 850, 900, 950, or 1000 μm, including ranges between any of the foregoing.

A thirty-ninth aspect is a nested permeable support device of any of aspects 30 to 38 further comprising a second well having a bottom at least partially defined by a second permeable support, and wherein the first well and the first permeable support are located below the second well and the second permeable support.

A fortieth aspect is a nested permeable support device of aspect 39 wherein the second well comprises a tapered shape.

A forty-first aspect is a nested permeable support device of any of aspect 30 to 40 wherein the bottom of the reservoir comprises a gas permeable material.

A forty-second aspect is a nested permeable support device comprising: (i) a first well having a bottom, wherein at least a portion of the bottom is formed by a first permeable support; (ii) a second well having a bottom, wherein the bottom of the second well comprises an arcuate shape and at least a portion of the bottom is formed by a second permeable support, and wherein the second well and the second permeable support are located below the first well and the first permeable support; and (ii) a third well having a bottom which is located below the second well and the second permeable support.

A forty-third aspect is a nested permeable support device of aspect 42 wherein at least a portion of the second well is coated with an ultra-low binding material.

A forty-fourth aspect is a cell culture insert comprising a body having a first open end, a second end, and one or more sidewalls extending from the first open end to the second end; and wherein the second end comprises a substrate having an array of microwells defining wells, wherein at least a portion of a substrate having an array of microwells defining a well is sloped.

A forty-fifth aspect is a cell culture insert of aspect 44 wherein the sidewalls are sloped.

A forty-sixth aspect is a cell culture insert of either of aspect 44 or 45 wherein the sidewalls are non-adherent to cells.

A forty-seventh aspect is a cell culture insert of any of aspects 44 to 46 wherein at least a portion of the substrate having an array of microwells is non-adherent to cells.

A forty-eighth aspect is a cell culture insert of any of aspects 44 to 47 wherein the wells have an inner surface defining an upper aperture and wherein the wells have a diametric dimension at the upper aperture in a range from 100 μm to 1000 μm.

A forty-ninth aspect is a cell culture insert of any of aspects 44 to 48 wherein the wells have a depth in a range from 100 μm to 100 μm.

A fiftieth aspect is a cell culture insert of any of aspects 44 to 49 wherein at least a portion of the substrate having an array of microwells is non-adherent to cells.

A fifty-first aspect is a cell culture insert of any of aspects 44 to 49 wherein at least a portion of the substrate having an array of microwells is adherent to cells.

A fifty-second aspect is a cell culture insert of any of aspects 44 to 51 wherein at least a portion of the substrate having an array of microwells is porous.

A fifty-third aspect is a cell culture insert of any of aspects 44 to 52 wherein the substrate having an array of microwells comprises openings.

A fifty-fourth aspect is a cell culture insert of any of aspects 44 to 53 wherein the substrate having an array of microwells is adhered to, affixed to, or juxtaposed with a porous membrane.

A fifty-fifth aspect is a cell culture insert of any of aspects 44 to 54 wherein the second end is covered by a porous membrane.

A fifty-sixth aspect is a cell culture insert of any of aspects 44 to 55 wherein the substrate having an array of microwells comprises a sloped surface.

A fifty-seventh aspect is a cell culture insert of any of aspects 44 to 56 wherein the substrate having an array of microwells comprises an array of hexagonal structures.

A fifty-eighth aspect is a cell culture assembly, comprising: (i) a reservoir defining an interior and having a bottom; and (ii) a first cell culture insert according to any one of aspects 44-57 configured to be positioned in the interior of the reservoir such that the second end of the body is above the bottom of the reservoir, wherein the body of the first insert defines an interior of the first insert.

A fifty-ninth aspect is a cell culture assembly according to aspect 58, wherein the interior of the first insert, when the first insert is positioned in the interior of the reservoir, is in fluid communication with the interior of the reservoir only through the porous membrane disposed over the opening of the second end of the body of the first insert.

A sixtieth aspect is a cell culture assembly according to aspect 58 or aspect 59, further comprising a second insert having a body defining an interior, the body comprising a first open end, a second end defining an opening, and one or more sidewalls extending from the first open end to the second end, wherein the second insert is configured to be positioned in the interior of the first insert such that the second end of the body of the second insert above the second end of the body of the first insert.

A sixty first aspect is a cell culture assembly according to aspect 60, wherein the interior of the second insert, when the second insert is positioned in the interior of the first insert, is in fluid communication with the interior of the first insert only through the porous membrane disposed over the opening of the second end of the body of the second insert.

A sixty second aspect is a cell culture insert comprising: a body sized for insert into a reservoir of a cell culture device, said body having a first open end, a second end having a porous membrane, and one or more sidewalls extending from the first open end to the second end; wherein the one or more sidewalls are sloped; and wherein said second end has an upper surface defining a plurality of microwells sized for spheroid growth.

A sixty third aspect is the cell culture insert of aspect 62, wherein said microwells each have a diameter in a range from 100 μm to 1000 μm.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred. Any recited single or multiple feature or aspect in any one claim can be combined or permuted with any other recited feature or aspect in any other claim or claims.

It is also noted that recitations herein refer to a component being "configured" or "adapted to" function in a particular way. In this respect, such a component is "configured" or "adapted to" embody a particular property, or function in a particular manner, where such recitations are structural recitations as opposed to recitations of intended use. More specifically, the references herein to the manner in which a component is "configured" or "adapted to" denotes an existing physical condition of the component and, as such, is to be taken as a definite recitation of the structural characteristics of the component.

While various features, elements or steps of particular embodiments may be disclosed using the transitional phrase "comprising," it is to be understood that alternative embodiments, including those that may be described using the transitional phrases "consisting" or "consisting essentially of," are implied. Thus, for example, implied alternative embodiments to a cell culture insert comprising body and a porous membrane include embodiments where a cell culture insert consists of a body and a porous membrane and embodiments where a cell culture insert consists essentially of a body and a porous membrane.

It will be apparent to those skilled in the art that various modifications and variations can be made to the present inventive technology without departing from the spirit and scope of the disclosure. Since modifications, combinations, sub-combinations and variations of the disclosed embodiments incorporating the spirit and substance of the inventive technology may occur to persons skilled in the art, the inventive technology should be construed to include everything within the scope of the appended claims and their equivalents In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The embodiments are not limited to the exact details shown and described, for variations obvious to one skilled in the art will be included within the embodiments defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters are approximations, the numerical values set forth in the specific examples are reported as precisely as possible. All numerical values, however, inherently contain a range necessarily resulting from the standard deviation found in their respective testing measurements.

Any direction referred to herein, such as "top," "bottom," "left," "right," "upper," "lower," "above," "below," and other directions and orientations are described herein for clarity in reference to the figures and are not to be limiting of an actual device or system or use of the device or system. Many of the devices, articles or systems described herein may be used in a number of directions and orientations. Directional descriptors used herein with regard to cell culture apparatuses often refer to directions when the apparatus is oriented for purposes of culturing cells in the apparatus.

The words "preferred" and "preferably" refer to embodiments that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments.

As used herein, "have", "has", "having", "include", "includes", "including", "comprise", "comprises", "comprising" or the like are used in their open ended inclusive sense, and generally mean "include, but not limited to", "includes, but not limited to", or "including, but not limited to".

"Optional" or "optionally" means that the subsequently described event, circumstance, or component, can or cannot occur, and that the description includes instances where the event, circumstance, or component, occurs and instances where it does not.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.). Ranges can be expressed herein as from "about" one particular value, and/or to "about" another particular value. When such a range is expressed, examples include from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

For any method disclosed herein that includes discrete steps, the steps may be conducted in any feasible order. And, as appropriate, any combination of two or more steps may be conducted simultaneously.

A number of abbreviations are used herein. A listing of some of those abbreviations and their meaning are presented below:
ADME-Tox—Absorption, Distribution, Metabolism, Excretion, and Toxicity
NBE—New Biological Entity
NCE—New Chemical Entity
TEER—Trans Epithelial Electrical Resistance All headings are for the convenience of the reader and should not be used to limit the meaning of the text that follows the heading, unless so specified.

What is claimed is:

1. A spheroid promoting cell culture insert comprising:
a first insert comprising:
a body sized for insert into a reservoir of a cell culture device, said body having a first open end, a second end defining a first opening having a first diametric dimension in a range from 200 μm to 750 μm, and one or more sidewalls extending from the first open end to the second end; wherein the one or more sidewalls comprise a lower sidewall portion proximate the second end, wherein the lower sidewall portion of the one or more sidewalls is sloped, the one or more sidewalls comprising a cell non-adherent material coating to promote cells cultured in the first insert to form spheroids; and
a porous membrane disposed over the opening of the second end, wherein the porous membrane comprises an array of microwells structured and arranged to form a spheroid in each microwell, wherein each microwell comprises a top aperture, a sidewall, and a porous membrane bottom, wherein the porous membrane bottom is non-adherent to cells, wherein a portion of a microwell of the array of microwells at least partially defines a spheroid confinement volume having a depth in a range from 100 μm to 500 μm;
wherein the first insert is configured to be positioned in an interior of the reservoir to retain the second end of the first insert above a bottom of the reservoir, wherein the porous membrane of the first insert has an arcuate shape; and
a second insert comprising:
a first open end of the second insert, a second end of the second insert defining a second opening of the second insert, the second opening having a second diametric dimension in a range from 200 μm to 750 μm, and one or more sidewalls of the second insert extending from the first open end of the second insert to the second end of the second insert, wherein the one or more sidewalls of the second insert comprise a lower sidewall portion of the second insert proximate the second end of the second insert, wherein the lower sidewall portion of the one or more sidewalls of the second insert is sloped, the one or more sidewalls of the second insert comprising a cell non-adherent material coating to promote cells cultured in the second insert to form spheroids;
wherein the second insert is configured to be positioned in an interior of the first insert to retain the second end of the second insert above the second end of the first insert.

2. The spheroid promoting cell culture insert of claim 1, wherein the interior of the first insert, when the first insert is positioned in the interior of the reservoir, is in fluid communication with the interior of the reservoir only through the porous membrane disposed over the opening of the second end of the first insert.

3. The spheroid promoting cell culture insert of claim 1, wherein the interior of the second insert, when the second insert is positioned in the interior of the first insert, is in fluid communication with the interior of the first insert only through the porous membrane disposed over the opening of the second end of the second insert.

4. The spheroid promoting cell culture insert of claim 3, wherein at least a portion of the reservoir is gas permeable.

5. A spheroid promoting cell culture insert comprising:
a body having a first open end, a second end wherein the second end defines an opening, and one or more sidewalls extending from the first open end to the second end, the one or more sidewalls comprising a cell non-adherent material coating to promote cells cultured in the insert to form spheroids;
wherein the one or more sidewalls comprise a lower sidewall portion proximate the second end, wherein the lower sidewall portion of the one or more sidewalls is sloped; and
a porous membrane disposed over the opening of the second end, wherein the porous membrane has an arcuate shape and comprises an array of microwells structured and arranged to form a spheroid in each microwell, wherein each microwell comprises a top aperture having a diametric dimension in a range from 200 µm to 500 µm, a sidewall, and a porous membrane bottom, wherein at least a portion of a microwell of the array of microwells comprises a conical shape to define a spheroid confinement volume, a depth in a range from 100 µm to 500 µm, and wherein the porous membrane bottom is non-adherent to cells.

6. A spheroid promoting cell culture insert comprising:
a body having a first open end, a second end, and one or more sidewalls extending from the first open end to the second end, the one or more sidewalls comprising a cell non-adherent material coating to promote cells cultured in the insert to form spheroids;
wherein the one or more sidewalls comprise a lower sidewall portion proximate the second end, wherein the lower sidewall portion of the one or more sidewalls is sloped; and
wherein the second end comprises a substrate having an array of microwells comprising an array of hexagonal structures, each microwell arranged to form a spheroid in each microwell, wherein each microwell comprises a top aperture having a diametric dimension in a range from 100 µm to 1000 µm, a sidewall, and a bottom, wherein a portion of a microwell of the array of microwells have a depth in a range from 100 µm to 500 µm to define a spheroid confinement volume, and wherein the bottom is non-adherent to cells.

7. The spheroid promoting cell culture insert of claim 6, wherein the substrate having an array of microwells comprises a sloped surface.

8. The spheroid promoting cell culture insert of claim 6, wherein at least a portion of the substrate having an array of microwells is porous.

9. The spheroid promoting cell culture insert of claim 6, wherein the substrate having an array of microwells comprises openings.

10. The spheroid promoting cell culture insert of claim 6, wherein the substrate having an array of microwells is adhered to, affixed to, or juxtaposed with a porous membrane.

11. The spheroid promoting cell culture insert of claim 6, wherein the second end is covered by a porous membrane.

* * * * *